US009649480B2

United States Patent
Sugimoto et al.

(10) Patent No.: US 9,649,480 B2
(45) Date of Patent: May 16, 2017

(54) DEVICES AND METHODS OF TREATING OR AMELIORATING DIASTOLIC HEART FAILURE THROUGH PULMONARY VALVE INTERVENTION

(71) Applicant: DC Devices, Inc., Tewksbury, MA (US)

(72) Inventors: Hiroatsu Sugimoto, Cambridge, MA (US); Christopher J. Magnin, Andover, MA (US)

(73) Assignee: CORVIA MEDICAL, INC., Tewksbury, MA (US)

( * ) Notice: Subject to any disclaimer, the term of this patent is extended or adjusted under 35 U.S.C. 154(b) by 523 days.

(21) Appl. No.: 13/937,177

(22) Filed: Jul. 8, 2013

(65) Prior Publication Data
US 2014/0012181 A1   Jan. 9, 2014

Related U.S. Application Data

(60) Provisional application No. 61/669,008, filed on Jul. 6, 2012.

(51) Int. Cl.
*A61M 27/00* (2006.01)
*A61F 2/24* (2006.01)
(Continued)

(52) U.S. Cl.
CPC ......... *A61M 27/002* (2013.01); *A61F 2/2436* (2013.01); *A61F 2/2445* (2013.01); *A61F 2/90* (2013.01); *A61F 2002/068* (2013.01)

(58) Field of Classification Search
CPC .................................. A61F 2/24; A61F 2/2454
See application file for complete search history.

(56) References Cited

U.S. PATENT DOCUMENTS 4,018,228 A   4/1977   Goosen
4,705,507 A   11/1987  Boyles
(Continued)

FOREIGN PATENT DOCUMENTS

EP   1470785   10/2004
EP   2537490   12/2012
(Continued)

OTHER PUBLICATIONS

Ad et al., "A one way valved atrial septal patch: A new surgical technique and its clinical application", The Journal of Thoracic and Cardiovascular Surgery, vol. 111, Apr. 1996, pp. 841-848.
(Continued)

*Primary Examiner* — Katherine M Shi
*Assistant Examiner* — Michael Mendoza
(74) *Attorney, Agent, or Firm* — Helen S. Liu

(57) ABSTRACT

The present teachings provide a device and methods of making and use thereof. Specifically, one aspect of the present teachings provides a device for restricting blood flow entering the lung after each right bean systole. Certain embodiments of the present teachings provide a device that prevents a complete closure of the pulmonary valve leaflets so that a certain amount of blood is allowed to flow from the pulmonary artery to the right ventricle at the end of a right ventricle systole. Other embodiments of the present teachings provide a device that restricts the amount of blood outflowing from the right ventricle to the pulmonary artery. In addition, the present teachings also provide a delivery system for implanting such a device approximately to or at the pulmonary valve.

13 Claims, 8 Drawing Sheets

(51) Int. Cl.
 *A61F 2/90* (2013.01)
 *A61F 2/06* (2013.01)

(56) References Cited

U.S. PATENT DOCUMENTS

| | | | |
|---|---|---|---|
| 5,108,420 A | 4/1992 | Marks | |
| 5,171,233 A | 12/1992 | Amplatz et al. | |
| 5,334,217 A | 8/1994 | Das | |
| 5,429,144 A | 7/1995 | Wilk | |
| 5,578,045 A | 11/1996 | Das | |
| 5,693,090 A | 12/1997 | Unsworth et al. | |
| 5,702,412 A | 12/1997 | Popov et al. | |
| 5,725,552 A | 3/1998 | Kotula et al. | |
| 5,824,071 A | 10/1998 | Nelson et al. | |
| 5,876,436 A | 3/1999 | Vanney et al. | |
| 6,050,936 A | 4/2000 | Schweich et al. | |
| 6,077,281 A | 6/2000 | Das | |
| 6,123,715 A | 9/2000 | Amplatz | |
| 6,156,055 A | 12/2000 | Ravenscroft | |
| 6,190,353 B1 | 2/2001 | Makower et al. | |
| 6,193,734 B1 | 2/2001 | Bolduc et al. | |
| 6,258,119 B1 | 7/2001 | Hussein et al. | |
| 6,334,864 B1 | 1/2002 | Amplatz et al. | |
| 6,350,277 B1 | 2/2002 | Kocur | |
| 6,355,052 B1 | 3/2002 | Neuss et al. | |
| 6,355,056 B1 | 3/2002 | Pinheiro | |
| 6,383,195 B1 | 5/2002 | Richard | |
| 6,395,017 B1 | 5/2002 | Dwyer et al. | |
| 6,402,777 B1 | 6/2002 | Globerman et al. | |
| 6,409,716 B1 | 6/2002 | Sahatjian et al. | |
| 6,440,152 B1 | 8/2002 | Gainor et al. | |
| 6,454,795 B1 | 9/2002 | Chuter | |
| 6,458,153 B1 | 10/2002 | Bailey et al. | |
| 6,468,303 B1 | 10/2002 | Amplatz et al. | |
| 6,527,746 B1 | 3/2003 | Oslund et al. | |
| 6,626,936 B2 | 9/2003 | Stinson | |
| 6,641,610 B2 | 11/2003 | Wolf et al. | |
| 6,645,143 B2 | 11/2003 | Van Tassel et al. | |
| 6,666,885 B2 | 12/2003 | Moe | |
| 6,712,836 B1 | 3/2004 | Berg et al. | |
| 6,837,901 B2 | 1/2005 | Rabkin et al. | |
| 6,866,679 B2 | 3/2005 | Kusleika | |
| 6,911,037 B2 | 6/2005 | Gainor et al. | |
| 6,913,614 B2 | 7/2005 | Marino et al. | |
| 6,936,058 B2 | 8/2005 | Forde et al. | |
| 6,979,343 B2 | 12/2005 | Russo et al. | |
| 7,001,409 B2 | 2/2006 | Amplatz et al. | |
| 7,097,653 B2 | 8/2006 | Freudenthal et al. | |
| 7,105,024 B2 | 9/2006 | Richelsoph | |
| 7,159,593 B2 | 1/2007 | McCarthy et al. | |
| 7,226,466 B2 | 6/2007 | Opolski | |
| 7,317,951 B2 | 1/2008 | Schneider et al. | |
| 7,338,514 B2 | 3/2008 | Wahr et al. | |
| 7,419,498 B2 | 9/2008 | Opolski et al. | |
| 7,445,630 B2 | 11/2008 | Lashinski et al. | |
| 7,473,266 B2 | 1/2009 | Glaser | |
| 7,485,141 B2 | 2/2009 | Majercak et al. | |
| 7,524,330 B2 | 4/2009 | Berreklouw | |
| 7,530,995 B2 | 5/2009 | Quijano et al. | |
| 7,625,392 B2 | 12/2009 | Coleman et al. | |
| 7,658,747 B2 | 2/2010 | Forde et al. | |
| 7,699,297 B2 | 4/2010 | Cicenas et al. | |
| 7,766,966 B2 | 8/2010 | Richelsoph | |
| 7,819,890 B2 | 10/2010 | Russo et al. | |
| 7,842,026 B2 | 11/2010 | Cahill et al. | |
| 7,871,419 B2 | 1/2011 | Devellian et al. | |
| 7,927,370 B2 | 4/2011 | Webler et al. | |
| 7,976,564 B2 | 7/2011 | Blaeser et al. | |
| 8,034,061 B2 | 10/2011 | Amplatz et al. | |
| 8,043,360 B2 | 10/2011 | McNamara et al. | |
| 8,048,147 B2 | 11/2011 | Adams | |
| 8,052,750 B2 * | 11/2011 | Tuval | A61F 2/2418 623/2.14 |
| 8,070,708 B2 | 12/2011 | Rottenberg et al. | |
| 8,091,556 B2 | 1/2012 | Keren et al. | |
| 8,157,860 B2 | 4/2012 | McNamara et al. | |
| 8,172,896 B2 | 5/2012 | McNamara et al. | |
| 8,252,042 B2 | 8/2012 | McNamara et al. | |
| 8,460,372 B2 | 6/2013 | McNamara et al. | |
| 2001/0029368 A1 | 10/2001 | Berube | |
| 2002/0029061 A1 | 3/2002 | Amplatz et al. | |
| 2002/0062135 A1 | 5/2002 | Mazzocchi et al. | |
| 2002/0072765 A1 | 6/2002 | Mazzocchi et al. | |
| 2002/0077698 A1 | 6/2002 | Peredo | |
| 2002/0082525 A1 | 6/2002 | Oslund et al. | |
| 2002/0082613 A1 | 6/2002 | Hathaway et al. | |
| 2002/0095172 A1 | 7/2002 | Mazzocchi et al. | |
| 2002/0095173 A1 | 7/2002 | Mazzocchi et al. | |
| 2002/0143289 A1 | 10/2002 | Ellis et al. | |
| 2002/0161424 A1 | 10/2002 | Rapacki et al. | |
| 2002/0161432 A1 | 10/2002 | Mazzucco et al. | |
| 2002/0165606 A1 | 11/2002 | Wolf et al. | |
| 2002/0169377 A1 | 11/2002 | Khairkhahan et al. | |
| 2002/0173742 A1 | 11/2002 | Keren et al. | |
| 2002/0177894 A1 | 11/2002 | Acosta et al. | |
| 2002/0183826 A1 | 12/2002 | Dom et al. | |
| 2002/0198563 A1 | 12/2002 | Gainor et al. | |
| 2004/0044351 A1 | 3/2004 | Searle | |
| 2004/0087937 A1 | 5/2004 | Eggers et al. | |
| 2004/0093075 A1 | 5/2004 | Kuehne | |
| 2004/0102719 A1 | 5/2004 | Keith et al. | |
| 2004/0111095 A1 | 6/2004 | Gordon et al. | |
| 2004/0133236 A1 | 7/2004 | Chanduszko et al. | |
| 2004/0143292 A1 | 7/2004 | Marino | |
| 2004/0162514 A1 | 8/2004 | Alferness et al. | |
| 2004/0176788 A1 | 9/2004 | Opolski | |
| 2004/0193261 A1 | 9/2004 | Berreklouw | |
| 2004/0206363 A1 | 10/2004 | McCarthy et al. | |
| 2004/0220653 A1 | 11/2004 | Borg et al. | |
| 2004/0236308 A1 | 11/2004 | Herweck et al. | |
| 2004/0243143 A1 | 12/2004 | Corcoran et al. | |
| 2004/0267306 A1 | 12/2004 | Blaeser et al. | |
| 2005/0049692 A1 | 3/2005 | Numamoto et al. | |
| 2005/0065548 A1 | 3/2005 | Marino et al. | |
| 2005/0065589 A1 | 3/2005 | Schneider et al. | |
| 2005/0070934 A1 | 3/2005 | Tanaka et al. | |
| 2005/0075655 A1 | 4/2005 | Bumbalough et al. | |
| 2005/0080400 A1 | 4/2005 | Corcoran et al. | |
| 2005/0148925 A1 | 7/2005 | Rottenberg et al. | |
| 2005/0165344 A1 | 7/2005 | Dobak | |
| 2005/0187616 A1 | 8/2005 | Realyvasquez | |
| 2005/0240205 A1 | 10/2005 | Berg et al. | |
| 2005/0267523 A1 | 12/2005 | Devellian et al. | |
| 2005/0273075 A1 | 12/2005 | Kulevitch et al. | |
| 2005/0288722 A1 | 12/2005 | Eigler et al. | |
| 2006/0004434 A1 | 1/2006 | Forde et al. | |
| 2006/0009715 A1 | 1/2006 | Khairkhahan et al. | |
| 2006/0009800 A1 | 1/2006 | Christianson et al. | |
| 2006/0122646 A1 | 6/2006 | Corcoran et al. | |
| 2006/0122647 A1 | 6/2006 | Callaghan et al. | |
| 2006/0136043 A1 | 6/2006 | Cully et al. | |
| 2006/0155305 A1 | 7/2006 | Freudenthal et al. | |
| 2006/0184088 A1 | 8/2006 | Van Bibber et al. | |
| 2006/0241745 A1 | 10/2006 | Solem | |
| 2006/0247680 A1 | 11/2006 | Amplatz et al. | |
| 2006/0253184 A1 | 11/2006 | Amplatz | |
| 2006/0276882 A1 | 12/2006 | Case et al. | |
| 2007/0016250 A1 | 1/2007 | Blaeser et al. | |
| 2007/0027528 A1 | 2/2007 | Agnew | |
| 2007/0038295 A1 | 2/2007 | Case et al. | |
| 2007/0043431 A1 | 2/2007 | Melsheimer | |
| 2007/0088388 A1 | 4/2007 | Opolski et al. | |
| 2007/0118207 A1 | 5/2007 | Amplatz et al. | |
| 2007/0123934 A1 | 5/2007 | Whisenant et al. | |
| 2007/0168019 A1 | 7/2007 | Amplatz et al. | |
| 2007/0185513 A1 | 8/2007 | Woolfson et al. | |
| 2007/0209957 A1 | 9/2007 | Glenn et al. | |
| 2007/0225759 A1 | 9/2007 | Thommen et al. | |
| 2007/0265658 A1 | 11/2007 | Nelson et al. | |
| 2007/0270741 A1 | 11/2007 | Hassett et al. | |
| 2007/0282157 A1 | 12/2007 | Rottenberg et al. | |
| 2008/0015619 A1 | 1/2008 | Figulla et al. | |
| 2008/0033425 A1 | 2/2008 | Davis et al. | |
| 2008/0033543 A1 | 2/2008 | Gurskis et al. | |

(56) References Cited

U.S. PATENT DOCUMENTS

| | | |
|---|---|---|
| 2008/0039804 A1 | 2/2008 | Edmiston et al. |
| 2008/0039922 A1 | 2/2008 | Miles et al. |
| 2008/0058940 A1 | 3/2008 | Wu et al. |
| 2008/0071135 A1 | 3/2008 | Shaknovich |
| 2008/0086168 A1 | 4/2008 | Cahill |
| 2008/0103508 A1 | 5/2008 | Karakurum |
| 2008/0119891 A1 | 5/2008 | Miles et al. |
| 2008/0125861 A1 | 5/2008 | Webler et al. |
| 2008/0154302 A1 | 6/2008 | Opolski et al. |
| 2008/0154351 A1 | 6/2008 | Leewood et al. |
| 2008/0172123 A1 | 7/2008 | Yadin |
| 2008/0183279 A1 | 7/2008 | Bailey et al. |
| 2008/0188888 A1 | 8/2008 | Adams et al. |
| 2008/0215008 A1 | 9/2008 | Nance et al. |
| 2008/0228264 A1 | 9/2008 | Li et al. |
| 2008/0249612 A1 | 10/2008 | Osborne et al. |
| 2008/0262592 A1 | 10/2008 | Jordan et al. |
| 2008/0312679 A1 | 12/2008 | Hardert et al. |
| 2009/0018562 A1 | 1/2009 | Amplatz et al. |
| 2009/0025820 A1 | 1/2009 | Adams |
| 2009/0030495 A1 | 1/2009 | Koch |
| 2009/0062841 A1 | 3/2009 | Amplatz et al. |
| 2009/0082803 A1 | 3/2009 | Adams et al. |
| 2009/0099647 A1 | 4/2009 | Glimsdale et al. |
| 2009/0112050 A1 | 4/2009 | Farnan et al. |
| 2009/0112244 A1 | 4/2009 | Freudenthal et al. |
| 2009/0131978 A1 | 5/2009 | Gainor et al. |
| 2009/0171386 A1 | 7/2009 | Amplatz et al. |
| 2009/0187214 A1 | 7/2009 | Amplatz et al. |
| 2009/0209855 A1 | 8/2009 | Drilling et al. |
| 2009/0210047 A1 | 8/2009 | Amplatz et al. |
| 2009/0210048 A1 | 8/2009 | Amplatz et al. |
| 2009/0234443 A1 | 9/2009 | Ottma et al. |
| 2009/0264991 A1 | 10/2009 | Paul et al. |
| 2009/0270840 A1 | 10/2009 | Miles et al. |
| 2009/0270909 A1 | 10/2009 | Oslund et al. |
| 2010/0022940 A1 | 1/2010 | Thompson |
| 2010/0023046 A1 | 1/2010 | Heidner et al. |
| 2010/0023048 A1 | 1/2010 | Mach |
| 2010/0023121 A1 | 1/2010 | Evdokimov et al. |
| 2010/0030321 A1 | 2/2010 | Mach |
| 2010/0049307 A1 | 2/2010 | Ren |
| 2010/0057192 A1 | 3/2010 | Celermajer |
| 2010/0063578 A1 | 3/2010 | Ren et al. |
| 2010/0094335 A1 | 4/2010 | Gerberding et al. |
| 2010/0106235 A1 | 4/2010 | Kariniemi et al. |
| 2010/0121370 A1 | 5/2010 | Kariniemi |
| 2010/0131053 A1 | 5/2010 | Agnew |
| 2010/0179491 A1 | 7/2010 | Adams et al. |
| 2010/0211046 A1 | 8/2010 | Adams et al. |
| 2010/0234881 A1 | 9/2010 | Blaeser et al. |
| 2010/0249909 A1 | 9/2010 | McNamara et al. |
| 2010/0249910 A1 | 9/2010 | McNamara et al. |
| 2010/0256548 A1 | 10/2010 | McNamara et al. |
| 2010/0256753 A1 | 10/2010 | McNamara et al. |
| 2010/0298755 A1 | 11/2010 | McNamara et al. |
| 2010/0324588 A1 | 12/2010 | Miles et al. |
| 2011/0004239 A1 | 1/2011 | Russo et al. |
| 2011/0004296 A1 | 1/2011 | Lutter et al. |
| 2011/0022079 A1 | 1/2011 | Miles et al. |
| 2011/0071623 A1 | 3/2011 | Finch et al. |
| 2011/0071624 A1 | 3/2011 | Finch et al. |
| 2011/0093062 A1 | 4/2011 | Cartledge et al. |
| 2011/0106149 A1 | 5/2011 | Ryan et al. |
| 2011/0112633 A1 | 5/2011 | Devellian et al. |
| 2011/0130784 A1 | 6/2011 | Kusleika |
| 2011/0190874 A1 | 8/2011 | Celermajer et al. |
| 2011/0213364 A1 | 9/2011 | Davis et al. |
| 2011/0218477 A1 | 9/2011 | Keren et al. |
| 2011/0218478 A1 | 9/2011 | Keren et al. |
| 2011/0218479 A1 | 9/2011 | Rottenberg et al. |
| 2011/0218480 A1 | 9/2011 | Rottenberg et al. |
| 2011/0218481 A1 | 9/2011 | Rottenberg |
| 2011/0257723 A1 | 10/2011 | McNamara et al. |
| 2011/0283871 A1 | 11/2011 | Adams |
| 2011/0295182 A1 | 12/2011 | Finch et al. |
| 2011/0295183 A1 | 12/2011 | Finch et al. |
| 2011/0295362 A1 | 12/2011 | Finch et al. |
| 2011/0295366 A1 | 12/2011 | Finch et al. |
| 2011/0306916 A1 | 12/2011 | Nitzan et al. |
| 2011/0307000 A1 | 12/2011 | Amplatz et al. |
| 2012/0053686 A1 | 3/2012 | McNamara et al. |
| 2012/0130301 A1 | 5/2012 | McNamara et al. |
| 2012/0165928 A1 | 6/2012 | Nitzan et al. |
| 2012/0259263 A1 | 10/2012 | Celermajer et al. |
| 2012/0265296 A1 | 10/2012 | McNamara et al. |
| 2012/0289882 A1 | 11/2012 | McNamara et al. |
| 2012/0290062 A1 | 11/2012 | McNamara et al. |
| 2013/0178783 A1 | 7/2013 | McNamara et al. |
| 2013/0178784 A1 | 7/2013 | McNamara et al. |
| 2013/0184633 A1 | 7/2013 | McNamara et al. |
| 2013/0184634 A1 | 7/2013 | McNamara et al. |
| 2013/0204175 A1 | 8/2013 | Sugimoto |
| 2013/0231737 A1 | 9/2013 | McNamara et al. |
| 2013/0267885 A1 | 10/2013 | Celermajer et al. |
| 2013/0281988 A1 | 10/2013 | Magnin |

FOREIGN PATENT DOCUMENTS

| | | |
|---|---|---|
| WO | 9527448 | 10/1995 |
| WO | 2008058940 | 5/2008 |
| WO | 2010111666 | 9/2010 |
| WO | 2014150106 | 9/2014 |

OTHER PUBLICATIONS

Althoff et al., "Long-Term Follow up of a Fenestrated Amplatzer Atrial Septal Occluder in Pulmonary Arterial Hypertension," Chest 2008, 133:183-85, 5 pages.

Atz et al., "Preoperative Management of Pulmonary Venous Hypertension in Hypoplastic Left Heart Syndrome With Restrictive Atrial Septal Defect", The American Journal of Cardiology, vol. 83, Apr. 15, 1999, pp, 1224-1228.

Bailey, "Nanotechnology in Prosthetic Heart Valves," approx. date 2005, presentation, 31 pages.

Bolling, "Direct Flow Medical—My Valve is Better," Apr. 23, 2009, presentation, 21 pages.

Cheatham, John P., "Intervention in the criticaily ill neonate and infant with hypoplastic left heart syndrome and intact atrial septum", Journal of Interventional Cardiology, vol. 14, No. 3, 2001, pp. 357-366.

Coselli, Joseph S., "No! valve replacement: patient prosthetic mismatch rarely occurs," Texas Heart Insitute, Apr. 25, 2009, 75 pages.

Design News, "Low Power Piezo Motion", http://www.designnews.com/document.asp?doc-id=229053&dfpPParams&dfpPParams=ht-13,aid-229053&dfpLayout=article, May 14, 2010, 3 pages.

European Application Serial No. EP10772411.4, European Search Opinion nd Supplementary European Search Report mailed Mar. 16, 2012, 5 pages.

European Application Serial No. EP12180631.9, European Search Report mailed Nov. 19, 2012, 5 pages.

Gaudiani et al., "A Philosophical Approach to Mitral Valve Repair," Apr. 24, 2009, presentation, 28 pages.

Hijazi, "Valve Implantation, Ziyad M. Hijazi," May 10, 2007, presentation, 36 pages.

International Application Serial No. PCT/AU2007/001704, International Preliminary Report on Patentability, mailed Aug. 22, 2008, 5 pages.

International Application Serial No. PCT/AU2007/001704, International Search Report, mailed Jan. 16, 2008, 4 pages.

International Application Serial No. PCT/AU2007/001704, Written Opinion, mailed Jan. 16, 2008, 5 pages.

International Application Serial No. PCT/US2010/026574, International Preliminary Report on Patentability, mailed Nov. 10, 2011, 6 pages.

International Application Serial No. PCT/US2010/020574, International Search Report, mailed Nov. 19, 2010, 5 pages.

(56) References Cited

OTHER PUBLICATIONS

International Application Serial No. PCT/US2010/058110, International Preliminary Report on Patentability, mailed Nov. 27, 2012, 7 pages.
International Application Serial No. PCT/US2010/058110, International Search Report and Written Opinion, mailed Aug. 26, 2011, 12 pages.
International Application Serial No. PCT/US2011/022895, International Search Report & Written Opinion, mailed Oct. 24, 2011, 10 pages.
International Application Serial No. PCT/US2011/041841, International Preliminary Report on Patentability and Written Opinion, mailed Jun. 6, 2013, 7 pages.
International Application Serial No. PCT/US2011/041841, International Search Report and Written Opinion, mailed Feb. 9. 2012, 10 pages.
International Application Serial No. PCT/US2012/024680, International Prelitninary Report on Patentability and Written Opinion, mailed Aug. 22, 2013, 6 pages.
International Application Serial No. PCT/US2012/024680, International Search Report and Written Opinion, mailed Oct. 23, 2012, 10 pages.
International Application Serial No. PCT/US2012/071588, International Search Report and Written Opinion, mailed Apr. 19, 2013, DC Devices, Inc., 17 pages.
Larios et al., "The Use of an Artificial Foraminal Valve Prosthesis in the Closure of Interatrial and Interventricular Septal Defects," Dis. Chest. 1959: 36; 631-41, 11 pages.
Leon, "Transoatheter Aortic Valve Therapy: Summary Thoughts," Jun. 24, 2009, presentation, 19 pages.
Merchant et al., "Advances in Arrhythmia and Electrophysiology; Implantable Sensors for Heart Failure", Circ. Arrhythm, Electrophysiol., vol, 3, Dec. 2010, pp. 657-667.
Moses, "The Good, the Bad and the Ugly of Transcatheter AVR," Jul 10, 2009, presentation, 28 pages.
O'Loughlin et al., "Insertion of a Fenestrated Arnpiatzer Atrial Sestosotomy Device for Severe Pulmonary Hypertension," Heart Lung Circ. 2006, 15(4):275-77, 3 pages.
Park et al., "Blade atrial septostomy: coliaborative study", Circulation, Journal of the American Heart Association, vol. 66, No. 2, Aug. 1982, pp. 258-266.
Pedra et al., "Stent Implantation to Create Interatrial Communications in Patients With Complex Congenital Heart Disease", Catheterintion and Cardiovascular Interventions 47, Jan. 27, 1999, pp. 310-313.
Perry et al., "Creation and Maintenance of an Adequate Interatrial Communicationin left Atrioventricular Valve Atresia or Stenosis", The American Journal of Cardiology, vol. 58, Sep. 15, 1986, pp. 622-626.
Philips et al., "Ventriculofemoroatrial shunt: a viable alternative for the treatment of hydrocephalus", J. Neurosurg., vol. 86, Jun. 1997, pp. 1063-1068.
Sommer et al., "Transcatheter Creation of Atrial Septal Defect and Fontan Fenestration with "Butterfly" Start Technique", Supplement to Journal of the American College of Cardiology, vol. 33, No. 2, Supplement A, Feb. 1999, 3 pages.
Stone, "Transcatheter Devices for Mitral Valve Repair, Surveying the Landscape," Jul. 10, 2009, presentation, 48 pages.
Stormer et al., "Comparative Study of in vitro Flow Characteristics between a Human Aortic Valve and a Designed Aortic Valve and Six Corresponding Types of Prosthetic Heart Valves," Eur. Surg. Res. 6: 117-131 (1976), 15 pages.
Watterson et al., "Very Small Pulmonary Arteries: Central End-to-Side Shunt", Ann. Thorac. Surg., vol. 52, No. 5, Nov. 1991, pp. 1132-1137.

\* cited by examiner

DEVICES AND METHODS OF TREATING OR AMELIORATING DIASTOLIC HEART FAILURE THROUGH PULMONARY VALVE INTERVENTION

CROSS-REFERENCE TO RELATED APPLICATION

The present application claims priority to and the benefit of U.S. Provisional Application Ser. No. 61/669,008, filed on Jul. 6, 2012, which is incorporated herein by reference in its entirety.

FIELD

The present teachings relate to devices and methods to treat or ameliorate diastolic heart failure by balancing the flow and pressure of the pulmonary valve. An example of the present teachings relates to a device that can be used to intervene or change (e.g., reduce) the blood pressure in a heart chamber by creating a shunt and optionally regulating the blood flow through the shunt to enhance the therapeutic effect of the shunt. The present teachings further relate to a method of utilizing such a device, for example, in treatment of congestive heart failure-related conditions, for example, acute cardiogenic pulmonary edema typically caused by an elevated pressure in a left side chamber in a heart.

BACKGROUND

The human circulatory system is a two-part system and its purpose is to bring oxygen-bearing blood to all tissues of the body. When a heart contracts, it pushes the blood out into two major loops or cycles. In the systemic loop, the blood circulates into the body's cardiovascular system, bringing oxygen to all the organs, structures, and tissues, and collecting carbon dioxide waste. In the pulmonary loop, the blood circulates to and from the lungs to exchange carbon dioxide for oxygen. The systemic cycle is controlled by the left side of the heart and the pulmonary cycle by the right side of the heart.

The systemic loop begins when the oxygen-rich blood coming from the lungs enters the left atrium of the heart. As the left atrium fills, it presses open the mitral valve and the blood flows down into the left ventricle. When the ventricles contract during, a heartbeat, the blood in the left ventricle is forced into the aorta. The blood leaving the aorta brings oxygen to all the body's cells through a network of smaller arteries and capillaries.

The oxygen-depleted blood from the body returns to the heart through a network of veins. All of the blood from the body is eventually collected into the two largest veins: the superior vena cava, which collects blood from the upper body, and the inferior vena cava, which collects blood from the lower body. Both the vena cava empty the blood into the right atrium of the heart. From here the blood begins its journey through the pulmonary cycle.

From the right atrium, the blood descends into the right ventricle through the tricuspid valve. When the right ventricle contracts, the blood is pushed through the pulmonary valve into the pulmonary artery that branches into two main parts: one going to the left lung, one to the right lung. The fresh, oxygen-rich blood returns to the left atrium of the heart through the pulmonary veins.

Although the circulatory system is made up of two cycles, both the cycles take place at the same time. The contraction of the heart muscle starts in the two atria, which push the blood into the two ventricles. Then the walls of the ventricles compress and force the blood out into the two arteries: the aorta to the body and the pulmonary artery to the lungs. Afterwards, the heart muscle, relaxes, allowing blood to flow in from the veins and fill the atria again.

Congestive heart failure (CHF) is a condition affecting millions of people worldwide. CHF results from a weakening or stiffening of the heart muscle that commonly is caused by myocardial ischemia (due to, e.g., myocardial infarction) or cardiomyopathy (e.g., myocarditis, amyloidosis). CHF causes reduced cardiac output and inadequate blood to meet the needs of body tissues. CHF is generally classified into systolic heart failures (SHF) or diastolic heart failures (DHF).

In a SHF, the pumping action of a heart is reduced or weakened. A normal ejection fraction (EF), which is a function of the volume of blood ejected out of the left ventricle (stroke volume) divided by the maximum volume remaining in the left ventricle at the end of the diastole or relaxation phase, is greater than 50%. In a systolic heart failure, EF is decreased to less than 50%. A patient with SHF may have an enlarged left ventricle because of cardiac remodeling developed to maintain an adequate stroke-volume. This pathophysiological phenomenon is often associated with increased atrial pressure and left ventricular filling pressure.

DHF is a heart failure refers to a decline in the performance of one of or both the ventricles of the heart during a diastole. Generally, DHF is a failure of the ventricle to adequately relax and expand, resulting in a decrease in the stroke volume of the heart. Thus, DHF is characterized by elevated diastolic pressure in the left ventricle, despite essentially normal/physiologic end diastolic volume (EDV). In a DHF patient, the stiffness of the left ventricular makes it more difficult for blood to enter it from the left atrium. As a result, pressure rises in the atrium and is transmitted back to the pulmonary venous system, thereby increasing its hydrostatic pressure and promoting pulmonary edema. DHF afflicts between 30% and 70% of those patients with CHF.

Presently, there are very few treatment options for patients suffering from DHF. Treatments for CHF include: (1) pharmacological treatments, (2) assisting systems, and (3) surgical treatments. Pharmacological treatments, e.g., with diuretics, are used to reduce the workload of as heart by reducing blood volume and preload. While drug treatment improves quality of life, it has little effect on survival. Assisting devices, e.g., mechanical pumps, are used to reduce the load on the heart by performing all or part of the pumping function normally done by the heart. However, in a chronic ischemic heart, a high-rate pacing may lead to increased diastolic pressure, calcium overload, and damage to the muscle fibers. There are at least three surgical procedures for treatment of a heart failure: (1) heart transplant. (2) dynamic cardiomyoplasty, and (3) the Batista partial left ventriculectomy. These surgical treatments are invasive and have many limitations.

There are several known techniques that can be used to treat various symptoms of DHF. Without attempting to characterize the following references, for example, U.S. Pat. No. 8,091,556 by Keren et al. discloses the use of an interatrial pressure relief shunt with a valve and a tissue affixation element at each end of the shunt; U.S. Pat. No. 8,043,360 by McNamara et al. discloses the use of an interatrial pressure vent to allow sufficient flow from the left atrium to the right atrium to relieve an elevated left atrial pressure and resulting patient symptoms; and United States Patent Application Publication No. 20050165344 by Dobak discloses a pressure relief system with an interatrial septal conduit and an emboli barrier or trap mechanism to prevent thrombi or emboli from crossing the conduit into the left sided circulation and causing cryptogenic strokes. Dobak also discloses a conduit with a one-way valve which directs blood flow from the left atrium to the right atrium.

The constantly evolving nature of heart failure represents a significant challenge for the treatment. Therefore, there is a need for novel and adaptable methods and devices for treating DHF, for example, by reducing the flow and/or the pressure in the pulmonary circulation system, and the pressure in the left atrium.

SUMMARY

The present teachings provide a pulmonary valve intervention device for restricting blood flow that enters the lung after each right heart systole. According to one embodiment of the present teachings, a pulmonary valve intervention device prevents the complete closure of the pulmonary valve leaflets so that a certain amount of the blood is allowed to hack flow from the pulmonary artery to the right ventricle at the end of the right ventricle systole. According to another embodiment of the present teachings, a pulmonary valve intervention device restricts the amount of the blood that flows from the right ventricle to the pulmonary artery at each right heart systole.

In one embodiment of the present teachings, the pulmonary valve intervention device has an elongated delivery configuration and an expanded deployed configuration. The device comprises a hollow body portion with a distal end and a proximal end. The distal end of the device is configured to be distal to the pulmonary valve annulus, the proximal end of the device is configured to be proximal to the pulmonary valve annulus, and the body portion of the device is configured to prevent the pulmonary valve from closing fully. Thus, the outflowing blood from the right ventricle flows through the device from its proximal end to its distal end and reaches the pulmonary artery.

In another embodiment of the present teachings, the pulmonary valve intervention device comprises a hollow body portion with a distal end and a proximal end. One of the distal end and proximal end of the device is larger than the other. The distal end of the device is configured to be distal to the pulmonary valve annulus, the proximal end of the device is configured to be proximal to the pulmonary valve annulus, and the body portion of the device is configured to prevent the pulmonary valve leaflets from closing fully.

In another embodiment of the present teachings, the pulmonary valve intervention device comprises a hollow body portion with a distal end and a proximal end. The proximal end of the device is larger than the distal end of the device. The device is configured to be proximal to the pulmonary valve, so that the outflowing blood from the right ventricle flows through the device from its proximal end to its distal end and reaches the pulmonary valve. And the distal end of the device is adapted to expand radially.

In another embodiment of the present teachings, a delivery system for percutaneously delivering a pulmonary valve intervention device comprises a delivery sheath, a delivery catheter and an implant device having a first elongated profile and a second expanded profile. The delivery sheath comprises a distal portion and a lumen. The delivery catheter is slidably positioned within the lumen of the delivery sheath. The device, in its first elongated profile, is also slidably disposed inside the lumen of the distal portion of the delivery sheath. The delivery catheter has a distal end that engages the proximal end of the device.

In yet another embodiment of the present teachings, a method of implanting a pulmonary valve intervention device comprises providing a delivery system with a delivery sheath, a delivery catheter and a device in its elongated profile slidably disposed within a lumen the delivery sheath. The delivery system is advanced through a right heart catherization procedure and reaches the pulmonary valve. The device is deployed at the treatment site. Upon the device being fully deployed, the device is detached from the delivery catheter. The delivery system is then removed from the body.

DETAILED DESCRIPTION

Figure 1:
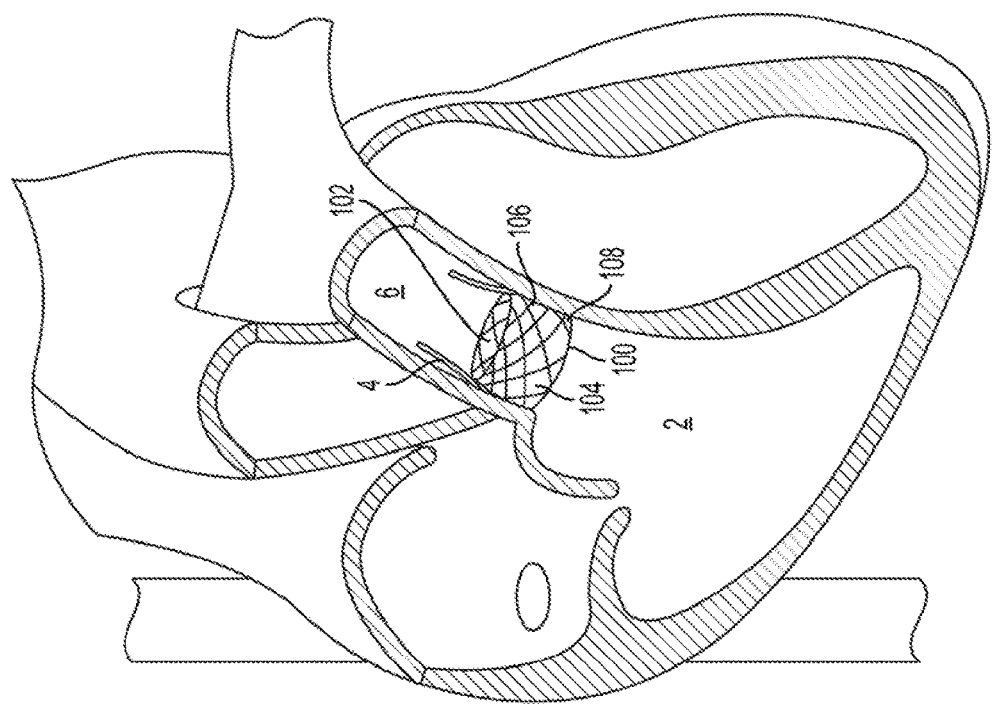
FIG. 1 is a perspective view of an exemplary medical device in accordance with the present teachings.

The present teachings provide devices and methods of use thereof. For example, the device can be used to reduce pressure inside the left atrium by manipulating the amount of blood flowing from the right ventricle through the pulmonary valve into the pulmonary artery. The present teachings are described more fully hereinafter with reference to the accompanying drawings, which show certain embodiments of the present teachings. The present teachings may, however, be embodied in many different forms and should not be construed as limited to the embodiments set forth herein; rather, these embodiments are provided to illustrate various aspects of the present teachings. Like numbers refer to like elements throughout.

As used herein the term "proximal" shall mean closest to the operator (less into the body) and "distal" shall mean furthest from the operator (further into the body). In positioning a medical device from a downstream access point, distal is inure upstream and proximal is more downstream.

The present teachings relate to a device with an elongated delivery profile, and an expanded deployed profile. As described in detail below, according to one embodiment, the device can have a straightened, elongated, low-profile delivery configuration suitable for delivery via a delivery system. The deployed configuration of the device can have a generally tubular configuration, can be radially expanded, or can sometimes be shortened in its overall length.

As explained in further detail be low, various embodiments of the present teachings provide medical devices for reducing the pressure in a left atrium of the heart. In some embodiments, the medical devices according to the present teachings may include a shunt, for example, a central lumen extending from the distal end of to the proximal end of the device, positioned through the pulmonary valve, thereby preventing the pulmonary valve from closing completely at the end of a ventricular systole cycle. In other embodiments, the medical devices according to the present teachings may restrict the amount of blood flowing from the right ventricle to the pulmonary valve.

According to one embodiment of the present teachings, the shunt of the device has a cross section in the shape of a circle, a polygonal such as square, or hexagonal, or other shapes suitable for the present application. In one embodiment of the present teachings, in its deployed configuration, the cross section of the device has a generally surface area of 15 mm$^2$ to 750 mm$^2$.

In one embodiment of the present teachings, the overall sizes of the cross sections of the device are reduced for delivery. According to one embodiment of the present teachings, the cross section of the device in the delivery profile is reduced to 10% to 90% of that in the deployed profile. In an alternatively embodiment, the cross section of the device remains the same during delivery and deployment.

In one embodiment of the present teachings, the total length of the device is elongated from the deployed configuration to the delivery configuration. According to one embodiment of the present teachings, the overall length of the deployed device is within the range of 10 mm to 150 mm. According to one embodiment of the present teachings, the overall length of the device, in its delivery profile, is 20% to 60% longer than its overall length in its deployed profile. In an alternative embodiment, the total length of the device in its delivery profile remains the same as its length in deployed profile.

In a pulmonary circulation, oxygen-depleted blood from the body leaves the systemic circulation when it enters the right atrium through the superior vena cava or the inferior vena cava. The blood is then pumped through the tricuspid valve into the right ventricle. The right ventricle fills. When the pressure in the right ventricle rises above the pressure in the pulmonary artery, as the right ventricle contracts, the pulmonary valve opens, and the blood inside the right ventricle is pushed through the pulmonary valve into the pulmonary artery in a ventricular systole. At the end of a ventricular systole, when the pressure in the right ventricle falls rapidly, the pressure in the pulmonary artery closes the pulmonary valve. The pulmonary valve is a one-way valve which, upon its closure, prevents blood from back flowing from the pulmonary artery to the right ventricle.

According to one embodiment of the present teachings, the pulmonary valve intervention device can restrict the amount of blood flowing from the right ventricle to the pulmonary artery, thereby reducing the amount of the blood that enters the lung. With a reduced amount of blood entering the lung, the amount of oxygen-enriched blood entering the left atrium is reduced, the left atrial pressure is reduced, and in turn the left ventricle pressure is reduced. This results in a left heart decompression during each pulmonary circulation. Additionally, with a reduced amount of blood entering the lung, the amount of oxygen-depleted bloods remaining inside the right ventricle increases, the right ventricle pressure increases, and the right atrial pressure increases.

According to one embodiment of the present teachings, the greater restriction is imposed by the pulmonary valve intervention device to the blood flow, the lesser amount of blood enters the lung, and in turn, the left atrium, and the greater the left heart decompresses. According to another embodiment of the present teachings, the less restriction is imposed by the pulmonary valve intervention device to the blood flow, the greater amount of blood enters the lung and the left atrium, and the lesser the left heart decompresses. The left atrial pressure can be measured directly with a catheter in the left atrium or indirectly by measuring the pulmonary capillary wedge pressure (PCWP), which can he measured during a right heart catheterization. As such, the normal values for the mean left atrial pressure are typically in the range of 6-12 mmHg. Thus, according to one embodiment of the present teachings, the restriction to blood flow imposed by the pulmonary valve intervention device is tailored so that, during and after an implantation, the left atrial pressure would reach the normal range of 6-12 mmHg. Thus for a DHF patient with a significantly elevated left atrial pressure, a pulmonary valve intervention device which imposes a great blood flow restriction should be used to restore the left atrial pressure to the normal range. For a DHF patient with a moderately elevated left atrial pressure, a pulmonary valve intervention device which imposes a moderate blood flow restriction should be used to restore the left atrial pressure to the normal range.

The left atrial v-wave is the left atrial pressure toward the end of an atrial diastole immediately preceding the opening of the mitral valve. The left atrial v-wave represents the peak of the left atrial pressure. The size of the left atrial v-wave is determined partially by the amount of blood entering the left atrium. The normal range of the left atrial v-wave is 6-21 mmHg. Thus, according, to one embodiment of the present teachings, the restriction to blood flow imposed by a pulmonary valve intervention device is tailored so that, during and after an implantation, the left atrial v-wave would reach the normal range of 6-21 mmHg. Thus for a DHF patient with a significantly elevated left atrial v-wave, a pulmonary valve intervention device which imposes a greater blood flow restriction should he used to restore the v-wave to the normal range. For a DHF patient presenting with a moderately elevated left atrial v-wave, a pulmonary valve intervention device which imposes a moderate blood flow restriction should be used to restore the v-wave to the normal range.

The systematic oxygen saturation is routinely monitored during a percutaneous implantation procedure. With the decompression of the left heart, according to one embodiment of the present teachings, the restriction to blood flow imposed by the pulmonary valve intervention device is tailored so that the systemic oxygen saturation level during and/or post implantation procedure is maintained in the range of 75-100%. Thus for a DHF patient with an elevated left atrial pressure, the higher is the left atrial pressure elevation pretreatment, the greater the restriction to blood flow by a pulmonary valve intervention device could be used while the systemic oxygen saturation level is maintained at its safe range; and the lower is the left atrial pressure elevation pretreatment, the smaller the restriction to blood flowing by a pulmonary valve intervention device could be used while the systemic oxygen saturation level is maintained at its safe range.

The ratio of the pulmonary blood flow to the systematic blood flow is defined as Qp:Qs ratio. In a healthy heart, the Qp:Qs ratio is 1:1. In a DHF patient, Qp:Qs ratio is generally greater than 1:1. Some goes beyond 2.5:1. With the implantation of a pulmonary valve intervention device, the Qp:Qs ratio could be restored to or close to the normal range. Thus, according to one embodiment of the present teachings, the restriction to blood flow imposed by the pulmonary valve intervention device is tailored so that, during and after an implantation, the Qp:Qs ratio would reach the acceptable range of 1:1 to 1.5:1 According to one embodiment of the present teachings, the greater is the Qp:Qs ratio pretreatment, the greater is the change to the Qp:Qs ratio during and after a treatment.

According to one embodiment of the present teachings, the greater is the restriction to blood flow imposed by a pulmonary valve intervention device, the lesser amount of blood enters the left atrium and in turn, the left ventricle. According to another embodiment of the present teachings, the lesser is the restriction to blood flow imposed by a pulmonary valve intervention device, the greater amount of blood enters the left atrium and, later, the left ventricle. The mean left ventricle pressure are typically in the range of 40-80 mmHg. Thus, according to one embodiment of the present teachings, the restriction to blood flow imposed by a pulmonary valve intervention device is tailored so that, during and after an implantation, the mean left ventricle pressure would reach the normal range of 40-80 mmHg. Thus for a DHF patient with a significantly elevated left ventricle pressure, a pulmonary valve intervention device which imposes a great blood flow restriction should be used to restore the mean left ventricle pressure to the normal range of 40-80 mmHg. For a DHF patient with a moderately elevated left ventricle pressure, a pulmonary valve intervention device which imposes a moderate blood flow restriction should be used to restore the left ventricle pressure to the normal range of 40-80 mmHg.

With the blood flow restricted by a pulmonary valve intervention device, the amount of oxygen-depleted blood remaining inside the right ventricle increases, which results in an elevated right ventricle peak systolic pressure. According to one embodiment of the present teachings, the greater is the restriction to blood flow, the greater amount of blood remains inside the right ventricle, and in turn, the greater is the elevation in the right ventricle peak systolic pressure. According to another embodiment of the present teachings, the lesser is the restriction to blood flow, the lesser amount of blood remains inside the right ventricle, and in turn, the lesser is the elevation in the right ventricle peak systolic pressure. The mean right ventricle peak systolic pressure are typically in the range of 20-40 mmHg. Thus, according to one embodiment of the present teachings, the restriction to the blood flow imposed by a pulmonary valve intervention device is tailored so that, during and after an implantation, the right ventricle peak systolic pressure would not exceed the normal range of 20-40 mmHg. Thus for a DHF patient with a right ventricle peak systolic pressure within a lower part of the range, such as in the range of 20-30 mmHg, a great restriction to blood flow can be imposed by a pulmonary valve intervention device; and for a DHF patient with a right ventricle peak systolic pressure within a higher part of the range, such as in the range of 30-40 mmHg, is moderate restriction to blood flow should be imposed by a pulmonary valve intervention device in order to prevent a right ventricle overload. According to yet another embodiment of the present teachings, the pulmonary valve intervention device is configured to reduce its restriction on blood flow as the right ventricle peak systolic pressure rises so that more blood and leave the right ventricle and flow through the pulmonary valve into the pulmonary artery. In one embodiment of the present teachings, the pulmonary valve intervention device is designed to completely abolish its restriction to blood flow when the right ventricle peak systolic pressure reaches a pre-defined maximum limit in order to prevent a right heart overload.

With the blood flow restricted by a pulmonary valve intervention device, the amount of oxygen-depleted blood remaining inside the right ventricle increases, the right ventricle peak systolic pressure increases, and in turn, the amount of blood remaining inside the right atrium increases, which results in an elevated right atrium pressure. According to one embodiment of the present teachings, the greater is the restriction to blood flow, the greater amount of the blood remains inside the right atrium, and in turn, the greater is the elevation in the right atrial pressure. According to another embodiment of the present teachings, the lesser is the restriction to blood flow, the lesser amount of the blood remains inside the right atrium, and in turn, the lesser is the elevation in the right atrial pressure. The normal values for the mean right atrial pressure are typically in the range of 4-12 mmHg. Thus, according to one embodiment of the present teachings, the restriction to blood flow imposed by a pulmonary valve intervention device is tailored so that, during, and after an implantation, the right atrial pressure does not exceed the range of 4-12 mmHg. Thus for a DHF patient with a right atrial pressure within a lower part of the range, such as in the range of 4-6 mmHg, a great restriction to blood flow can be imposed by a pulmonary valve intervention device; and for a DHF patient with a right atrial pressure within a higher part of the range, such as in the range of 10-12 mmHg, a moderate restriction to blood flow should be imposed by a pulmonary valve intervention device in order to prevent a right atrium overload. According to yet another embodiment of the present teachings, the pulmonary valve intervention device is configured to reduce its restriction on blood flow as the right atrial pressure rises so that more blood could leave the right ventricle and flow through the pulmonary valve into the pulmonary artery. In one embodiment of the present teachings, the pulmonary valve intervention device is designed to completely abolish its restriction to blood flow when the right atrial pressure reaches a pre-defined maximum limit in order to prevent a right heart overload.

With the blood flow restricted by a pulmonary valve intervention device, the amount of oxygen-depleted blood remaining inside the right ventricle increases, the right ventricle peak systolic pressure increases, and in turn, the pressure differential between the right ventricle and the pulmonary artery immediately before a right ventricle systole rises. According to one embodiment of the present teachings, the greater is the restriction to blood flow, the greater amount of oxygen-depleted blood remains insider the right ventricle, the greater is the pressure differential between the right ventricle and the pulmonary artery immediately before a right ventricle systole. According to another embodiment of the present teachings, the smaller is the restriction to blood flow, the lesser amount of blood remains inside the right ventricle, the lesser pressure differential is between the right ventricle and the pulmonary artery immediately before a right ventricle systole. The pressure differential between the right ventricle and the pulmonary artery immediately before a right ventricle systole are typically in the range of 2-10 mmHg. Thus, according to one embodiment of the present teachings, the restriction to blood flow imposed by the pulmonary valve intervention device is tailored so that, during and after an implantation, the pressure differential between the right ventricle and the pulmonary artery immediately before a right ventricle systole would not exceed the range of 2-10 mmHg. Thus for a DHF patient with a pressure differential between the right ventricle and the pulmonary artery immediately before a right ventricle systole within a lower part of the range, such as in the range of 2-5 mmHg, a great restriction, to blood flow can be imposed by a pulmonary valve intervention device; and for a DHF patient with a pressure differential between the right ventricle and the pulmonary artery immediately before a right ventricle systole within a higher part of the range, such as in the range of 5-10 mmHg, a moderate restriction to blood flow should be imposed by a pulmonary valve intervention device in order to prevent a right atrium overload. According to yet another embodiment of the present teachings, the pulmonary valve intervention device is configured to reduce its restriction on blood flow as the pressure differential between the right ventricle and the pulmonary artery immediately before a right ventricle systole rises so that more blood could leave the right ventricle and flow through the pulmonary valve into the pulmonary artery. In one embodiment of the present teachings, the pulmonary valve intervention device is designed to completely abolish its restriction to blood flow when the pressure differential between the right ventricle and the pulmonary artery immediately before a right ventricle systole reaches a pre-defined maximum limit in order to prevent a right heart overload.

As illustrated and explained in detail, all embodiments of the present teachings have an elongated delivery configuration and a radially expanded deployed configuration. According to one embodiment, a pulmonary valve intervention device, in its deployed configuration, has a generally tubular body with a distal end and a proximal end. The surface of the tubular body has a pre-cut or pre-formed pattern which is configured to allow a radially expansion or contraction of the device for the percutaneous delivery and deployment. Specifically, upon deployed at a treatment site, the device expands radially, and the pre-cut or pre-formed pattern on the tubular surface of the device creates an open-mesh structure with a hollow area to allow blood flow from one side of the tubular surface to the other. According to one embodiment of the present teachings, the size of each opening on the tubular surface of the device ranges from 1 mm$^2$ to 5 mm$^2$. According to another embodiment of the present teachings, the opening area consists of 50-95% of entire tubular surface of the device.

In some embodiments of the present teachings, the pre-cut or pre-formed pattern on the tubular surface of the pulmonary valve intervention device is fabricated by laser-cutting or acid-etching a pattern onto a preformed tube. In other embodiments, the pre-cut or pre-formed pattern on the tubular surface of the device is fabricated by slotting using, for example, a machining laser or water drill or other method and then expanded to farm the open structure. Such preformed tube is then shape-set to the intended deployed configuration. Alternatively the pre-cut or pre-formed pattern on the tubular surface of the device is fabricated by cutting a pattern from sheet. Such preformed sheet is then rolled up and welded or crimped at specific strut locations.

In another embodiment, the pulmonary valve intervention. device can be formed crow wires that are pre-hem into the desired shape and then bonded together to connect elements either by cross-hatching, braiding, welding, or other methods of interconnecting rows of metal that are assembled into a tube-like structure. In one embodiment, the wires could be welded using a resistance welding technique or an arc welding technique, preferably while in an inert gas environment and with cooling to control the grain structure in and around the weld site. These joints can be conditioned alter the welding procedure to reduce grain size using coining or upset forging to an optimal fatigue performance.

In one embodiment of the present teachings, where the pulmonary valve intervention device is made of an elastic and resilient material such as stainless steel, or nitinol, the structure of the device can be preformed into its deployed shape, and then elastically deformed and stowed during delivery so that the shape of the device would elastically recover after deployment. In another embodiment of the present teachings, where the device is made of a pseudoelastic shape-memory material such as nitinol, the device is manually expanded to the desired deployed size, heat set in an oven while constrained to the desired shape to memorize the desired device shape.

According to one embodiment of the present teachings, at least one portion of the pulmonary valve intervention device expands upon deployment in vivo. In one embodiment of the present teachings, upon deployment, the device expands radially due to the elastic nature of the material. In another embodiment, such radial expansion is achieved by the pre-set thermal shape memory of the device material. In yet another embodiment, such radial expansion is achieved manually via an inflating balloon.

In the embodiment of the presenting teachings where the pulmonary valve intervention device is expanded in vivo via a balloon, the device can be mounted over a balloon catheter, where the inflatable balloon is positioned inside the tubular body of the device. Upon deployment of the device at the treatment site, the balloon is then inflated, and the inflated balloon expands the shunt portion of the device to a desired size. Then, the balloon is deflated and retracted out of the tubular body of the device.

According to one embodiment of the present teachings, a deployed pulmonary valve intervention device is configured to secure itself against the surrounding tissues. In one embodiment, the device is secured at the treatment site by a radial interference force. In this embodiment, the pre-fabricate configuration of at least a portion of the deployed device has a greater radial dimension than the interior of the treatment location which produces an interference fit between the device and the surrounding tissue. According, to another embodiment of the present teachings, the device has at least one tissue anchor configured to secure the device against the surrounding tissues. Such tissue anchor can reduce relative movements of the device against the surrounding tissue, reduce the chance of device embolization, and/or reduce tissue abrasion against the device.

In one embodiment of the present teachings, the distal end of the pulmonary valve intervention device has a tissue anchor protruding radially outward from the device toward the surrounding heart tissue. In another exemplary of the present teachings, the proximal end of the device has a tissue anchor protruding radially outward from the device toward the surrounding heart tissues. The tissue anchors engage the surrounding heart tissue so that the device can be held in place thereby reducing the chance of device embolization. In one embodiment of the present teachings, the exemplary device has at least one tissue anchor near or at its distal end. In another embodiment, the device has at least one tissue anchor near or at its proximal end. In another embodiment, the device has at least one tissue anchor near or at each of its distal and proximal ends. In other embodiment, the device has multiple tissue anchors along its tubular surface configured to secure the device to the treatment location. For example, the tissue anchor of the device secures the device against the tissue inside the right ventricle outflow track, the tissue anchor of the device secures the device against the tissue inside the right ventricle, the tissue anchor of the device secures the device against the tissue of the pulmonary valve, the tissue anchor of the device secures the device against the tissue inside the pulmonary artery, etc. It should be understood by those with ordinary skill in the art that location of the tissue anchor on the device, and securement location by the tissue anchor against the tissue varies depending on the treatment site, size of the device, and needs for securement. In one embodiment of the present teachings, the tissue anchor could be a hook, a grasper, a loop, a ring, a spine, a tine, a helix, a barb, a clip, or one or more other features known to those skilled in the art, in one embodiment, the tissue anchor secures the device by penetrating into tissue around the exterior of the tubular surface.

According to one embodiment of the present teachings, the pulmonary valve intervention device in whole or certain portion(s) thereof may be made of a biocompatible metal or polymer. In some embodiments, the device in whole or certain portion(s) thereof is made of an elastic material, super-elastic material, or shape-memory alloy which allows said portions to distort into a generally straightened elongated profile during the delivery process and resume and maintain its intended profile in vivo once it is deployed from the delivery catheter. In some embodiments, the device is made of stainless steel, nitinol, Titanium, Elgiloy, Vitalium, Mobilium, Ticonium, Platinore, Stellite, Tantalum, Platium, Hastelloy, CoCrNi alloys (e.g., trade name Phynox), MP35N, or CoCrMo alloys or other metallic alloys. Alternatively, in such embodiments, a part or the entire device is made of a polymer such as PTFE, UHMPE, HDPE, polypropylene, polysulfone, or other biocompatible plastic. The surface finish of the device is textured to induce tissue responses and tissue in-growth for an improved stabilization. Alternatively, part or all of the device can he fabricated from a resort polymer such as polyactic acid, polyglycolic acid, polycaprolactone, a combination of two or more of these or a variety of other resorbable polymers that are known to those skilled in the art.

According to one embodiment of the present teachings, a radioopaque marker is used to make the device visible using radiographic imaging equipments such as X-ray, magnetic resonance, ultrasound or other imaging equipments. Marker as disclosed herein may be applied to any part of the device, or even on the delivery system of the device. A radioopaque marker can be sewed, adhered, swaged riveted, otherwise placed and secured on the device. The radioopaque marker may he made of tantalum, tungsten, platinum, irridium, gold, alloys of these materials or other materials that are known to those skilled in the art. The radioopaque marker can also he made of cobalt, fluorine or numerous other paramagnetic materials or other MR visible materials that are known to those skilled in the arts.

Now referring to FIG. 1, according to one embodiment of the present teachings, an exemplary pulmonary valve intervention device (100) is deployed at the pulmonary valve (4). As illustrated in FIG. 1, in its deployed configuration, the pulmonary valve intervention device (100) has a generally elongated tubular body (106), a distal end (102), a proximal end (104), and a shunt lumen (108) extending along the elongated body (106) from the distal end (102) to the proximal end (104). The elongated tubular body (106) of the device (100) has an open-mesh like surface which allows blood flow from one side of the tubular surface to the other.

According to one embodiment of the present teachings, the pulmonary valve intervention device (100) is deployed at a location that keeps the pulmonary valve (4) open during each pulmonary circulation. By preventing the pulmonary valve from closing completely, the blood is allowed to back flow from the pulmonary artery to the right ventricle. Such an exemplary device limits the amount of blood entering the lung from the pulmonary artery by allowing some amount of blood to back-flow through the shunt lumen (108) of the device (100) from the pulmonary artery (6) to the right ventricle (2) through an open pulmonary valve (4) when the pressure inside the pulmonary artery is greater than the pressure inside the right ventricle. During a pulmonary circulation, as the oxygen-depleted blood fills the right ventricle (2), the pressure of the right ventricle (2) rises above the pressure in the pulmonary artery (6). As the right ventricle (2) contracts, the oxygen-depleted blood in the right ventricle (2) is pushed through the pulmonary valve (4) into the pulmonary artery (6). As blood empties from the right ventricle (2), the pressure of the right ventricle (2) drops, and as the blood fills the pulmonary artery (6), the pressure inside the pulmonary artery (6) rises. While the pulmonary valve (4) is held open by the device (100), some amount of the blood would back-flow from the pulmonary artery (6) through the shunt lumen (108) of the device (100) to the right ventricle (2) as the pressure inside the pulmonary artery (6) rises. Thus the intervention with the pulmonary valve intervention device (100) leads to a reduced amount of oxygen-depleted blood entering the lung.

Figure 2:
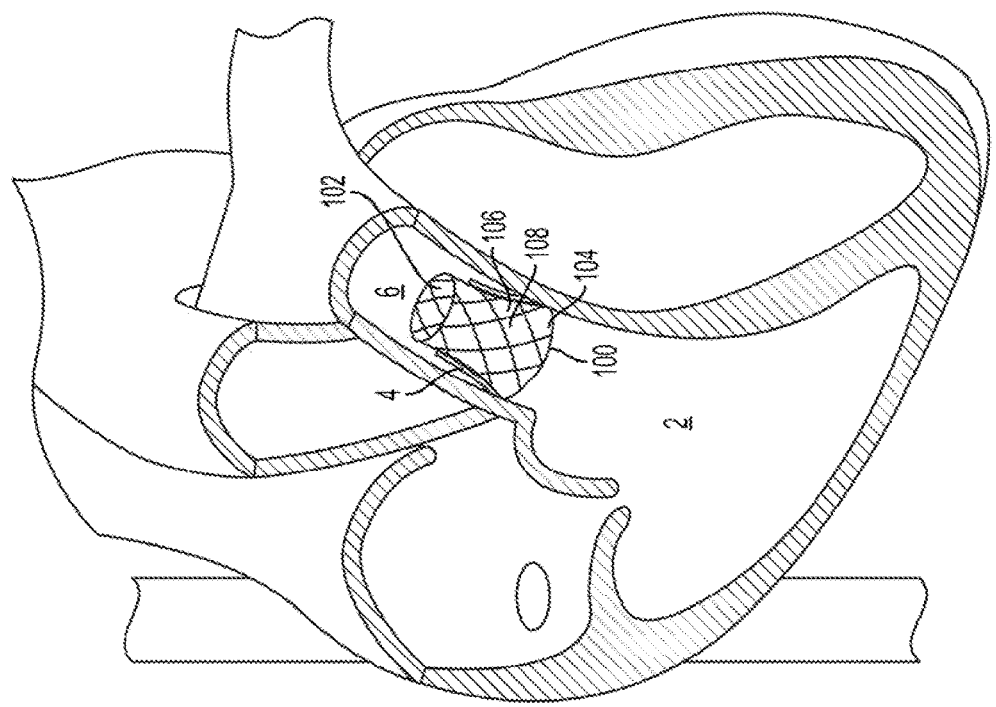
FIG. 2 is a perspective view of an exemplary medical device in accordance with the present teachings.
Figure 3:
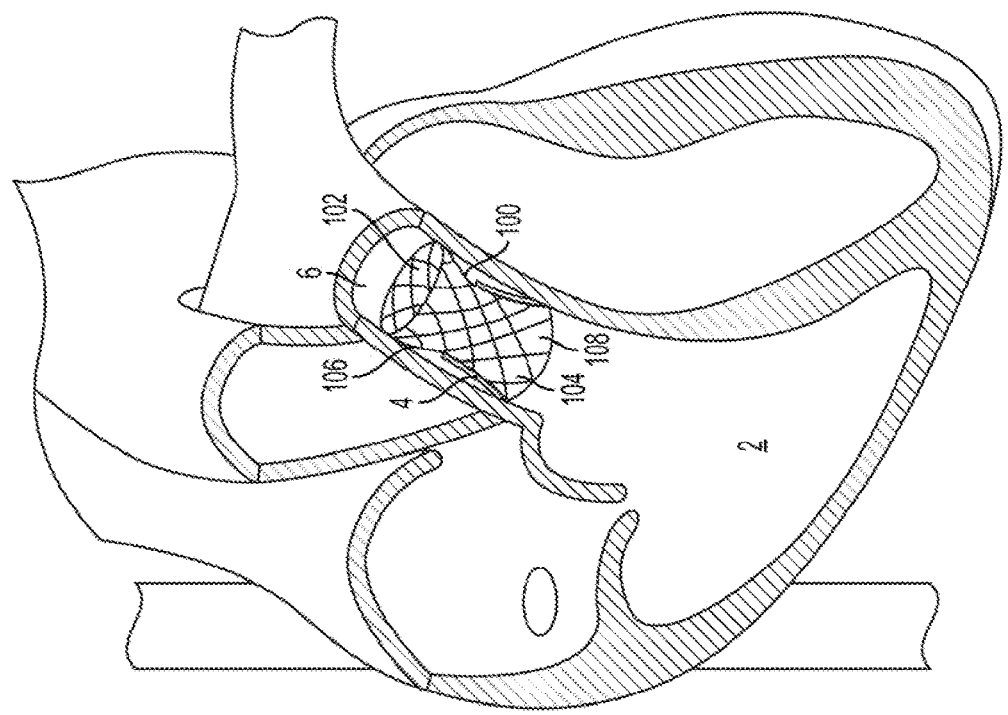
FIG. 3 is a perspective view of an exemplary me heal device in accordance with the present teachings.

In one embodiment, as illustrated in FIG. 1, the distal end (102) of the device (100) is positioned distally to the pulmonary valve (4) annulus, and the proximal end (104) of the device (100) is positioned proximally to the pulmonary valve (4) annulus, and the pulmonary valve leaflets are held open by the tubular body of the device (100). In another embodiment, as illustrated in FIG. 2, the distal end (102) of the device (100) is positioned at or approximate to the pulmonary valve (4) annulus, and the proximal end (104) of the device (100) is positioned proximal to the pulmonary valve (4) annulus, while the pulmonary valve leaflets are held open by the distal portion of the device (100). In another embodiment, as illustrated in FIG. 3, the distal end (102) of the device (100) is positioned distally to the pulmonary valve (4) annulus, and the proximal end (104) of the device (100) is positioned at or near the pulmonary valve (4) annulus, while the pulmonary valve leaflets are held open by the distal portion of the device (100).

According to one embodiment, the elongated tubular body (106) of the device (100) has a generally cylindrical shape. In another embodiment, the elongated tubular body (106) of the device (100) has a generally conical shape, with a smaller distal end (102), a greater proximal end (104), and a tapered body (106) extending from the distal end (102) to the proximal end (104). In another embodiment, the elongated tubular body (106) of the device (100) has a generally conical shape, with a greater distal end (102), a smaller proximal end (104), and a tapered body (106) extending from the distal end (102) to the proximal end (104). In other embodiments of the present teachings, the device (100) has other configurations each adapted to conform to the anatomy of the treatment location. In one embodiment, the device (100) has a generally circular cross section. In another embodiment, the cross section of the device (100) is in the shape of a polygon. In yet another embodiment of the present teachings, the cross section of the device (100) has other shapes adapted to confirm to the anatomy of the treatment location. In one embodiment, the device (100) has a uniform cross section throughout its length in another embodiment, the shape and size of the cross section of the device (100) varies at different sections.

Figure 4:
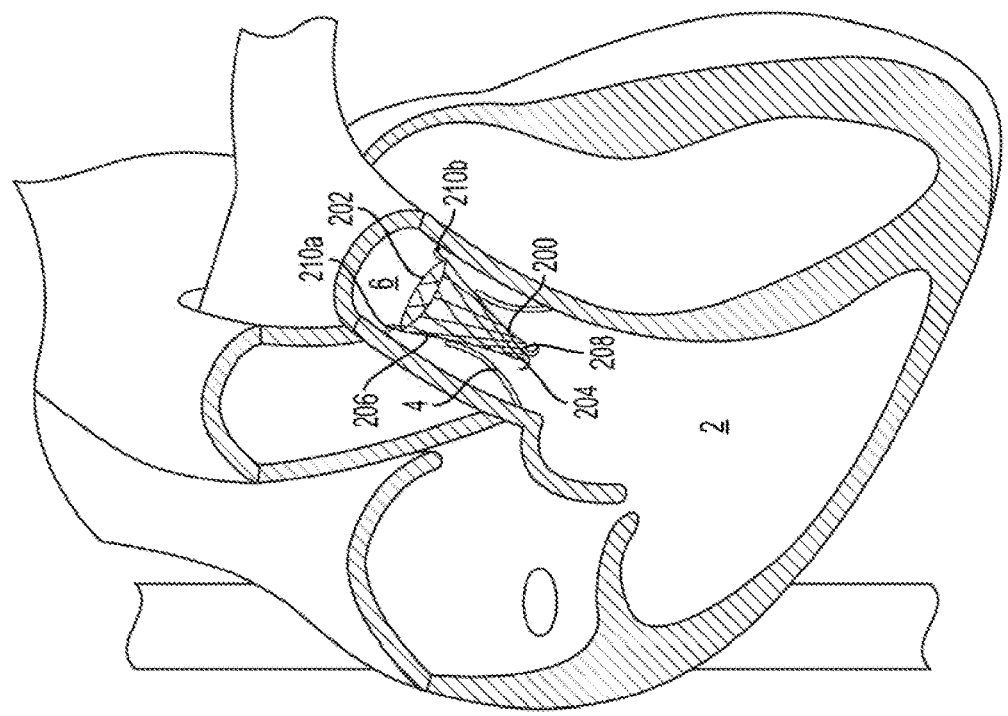
FIG. 4 is a perspective view of an exemplary medical device as the right ventricle pressure higher than the pulmonary artery pressure in accordance with the present teachings.
Figure 5:
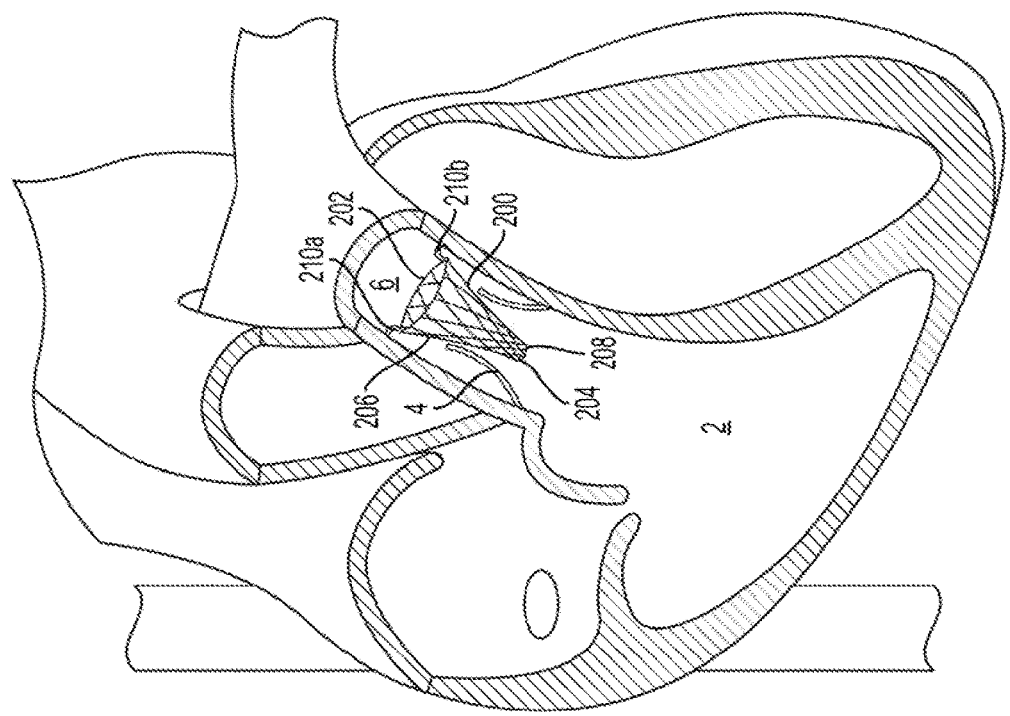
FIG. 5 is a perspective view of an exemplary medical device as the pulmonary artery pressure higher than the right ventricle pressure in accordance with the present teachings.

Now referring to FIGS. 4-5, an exemplary pulmonary valve intervention device (200) is deployed at the pulmonary valve (4). The device (200) has a distal end (202) having a diameter and positioned distally to the pulmonary valve (4) annulus, and a proximal end (204) having a diameter smaller than the diameter of the distal end and positioned proximally to the pulmonary valve (4) annulus. The tubular body of the device (200) is positioned through the pulmonary valve (4) while keeping the valve leaflets open. The device (200) has a tapered elongated tubular body (206) between the distal end (202) and the proximal end (204), and a shunt lumen (208) extending along the elongated body (206) from the distal end (202) to the proximal end (204). The pulmonary valve (4) is held open by the elongated tubular body of the device (200) to a predetermined degree. As the pressure inside the right ventricle (2) rises, and the right ventricle (2) contracts, the leaflets of the pulmonary valve (4) is pushed further open by the right ventricle pressure, as illustrated in FIG. 5. As the blood enters the pulmonary artery (6), the pressure inside the right ventricle (2) drops, and the pressure inside the pulmonary artery (6) rises, the leaflets of the pulmonary valve (4) is then pushed close by the pulmonary artery pressure to the extent that the device (200) allows, as illustrated in FIG. 4. Since the pulmonary valve (4) is held open by the elongated tubular body (206) of the device (200) to a predetermined degree, some amount of blood that entered the pulmonary artery back flows from the pulmonary artery (6) through the shunt lumen (208) of the device (200) to the right ventricle (2).

Figure 6:
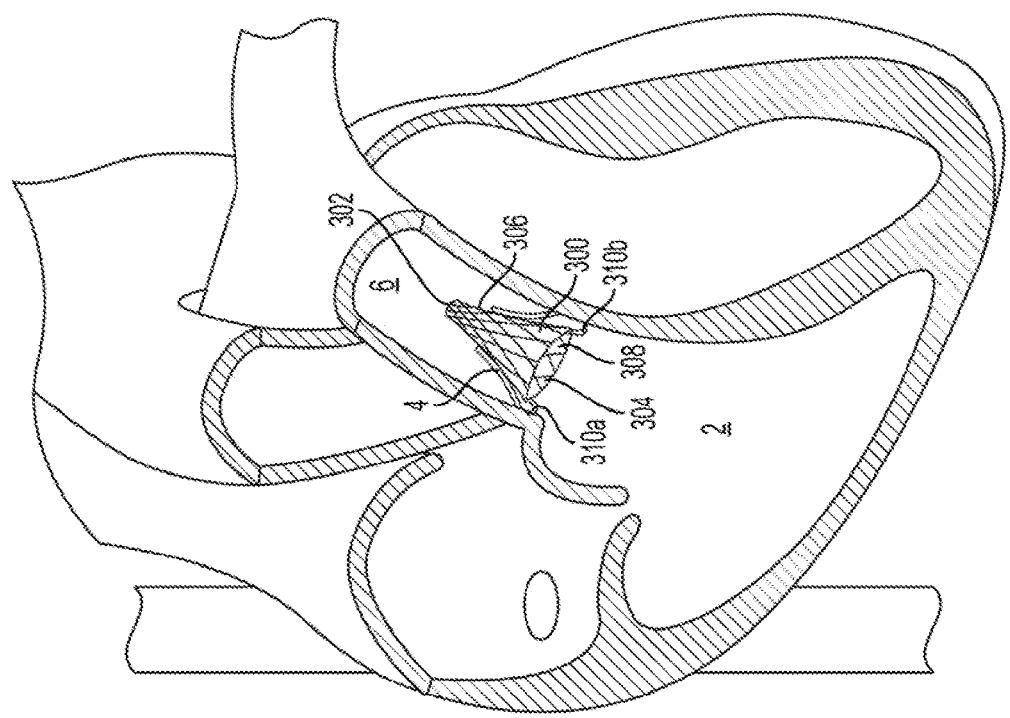
FIG. 6 is a perspective view of an exemplary medical device as the right ventricle pressure higher than the pulmonary artery pressure in accordance with the present teachings.
Figure 7:
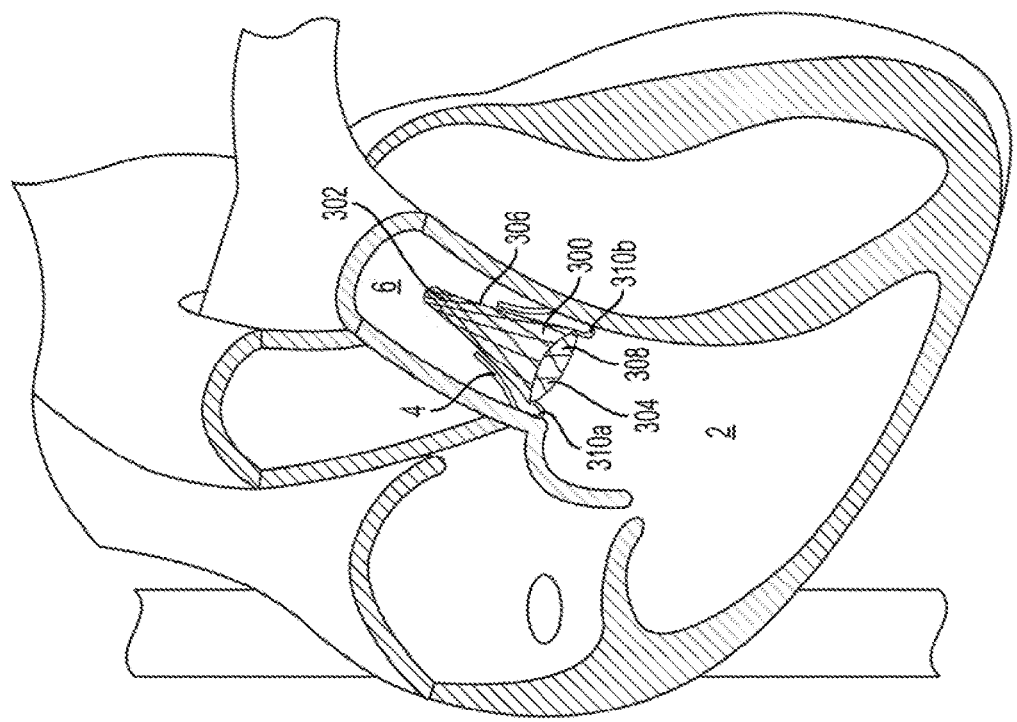
FIG. 7 is a perspective view of an exemplary medical device as the pulmonary artery pressure higher than the right ventricle pressure in accordance with the present teachings.

Now referring to FIGS. 6-7, an exemplary pulmonary valve intervention device (300) is deployed at the pulmonary valve (4). The device (300) has a proximal end (304) having a diameter and positioned proximally to the pulmonary valve (4) annulus, a distal end (302) having a diameter smaller than the diameter of the proximal end and positioned distally to the pulmonary valve (4) annulus, and the tubular body of the device (300) is positioned through the pulmonary valve (4) while keeping the valve leaflets open. The device (300) has a tapered elongated tubular body (306) between the distal end (302) and the proximal end (304), and a shunt lumen (308) extending along the elongated body (306) from the distal end (302) to the proximal end (304). The pulmonary valve (4) is held open b the elongated tubular body (306) of the device (300) to a predetermined degree. As the pressure inside the right ventricle (2) rises, and the right ventricle (2) contracts, the leaflets of the pulmonary valve (4) is pushed further open by the right ventricle pressure, as illustrated in FIG. 7. As the blood enters the pulmonary artery (6), the pressure inside the right ventricle (2) drops, and the pressure inside the pulmonary artery (6) rises, the Ica nets of the pulmonary valve (4) is then pushed close by the pulmonary artery pressure, to the extent that the device (300) allows, as illustrated in FIG. 6. Since the pulmonary valve (4) is held open by the device (300) to as predetermined degree, some blood then back flows from the pulmonary artery (6) to the right ventricle (2) through the shunt (308) of the device.

Referring to both FIGS. 4 and 6, the leaflets of the pulmonary valve (4) are prevented from fully closed at the end of each ventricular systole by the implantation of a pulmonary valve intervention device (200, 300). Such predetermined degree of opening is controlled by the tubular size of the elongated body of the device (200, 300), and the positioning of the device (200, 300) related, to the pulmonary valve (4) since the tubular body of the device (200, 300) are tapered from one end to the other. In one embodiment, the smaller is the size of the tubular body of the device (200, 300), the smaller is the opening between the leaflets; and the greater is the size of the tubular body of the device (200, 300), the larger is the opening between the leaflets. In another embodiment, the smaller is the size of the portion being positioned through the pulmonary valve, the smaller is the opening between the leaflets; and the greater is the size of the portion being positioned through the pulmonary valve, the greater is the opening between the leaflets.

In one embodiment, as the size of the portion of the device (200, 300) holding the leaflets of the pulmonary valve (4) open increases, the amount of the blood flowing hack from the pulmonary artery (6) to the right ventricle (2) through the shunt (208, 308) of the device (200, 300) increases, the amount of blood entering the lung decreases, the blood flow restriction imposed by such device (200, 300) thus increases, and then the degree of the left heart decompression increases. In another embodiment, as the size of the portion of the device (200, 300) held the leaflets of the pulmonary valve (4) open decreases, the amount of the blood flowing from the pulmonary artery (6) to the right ventricle (2) through the shunt (208, 308) decreases, the amount of blood entering the lung increases, the blood flow restriction imposed by such device (200, 300) thus decreases, and then the degree of the left heart decompression decreases.

Referring back to FIGS. 4-7, the devices (200, 300) have tissue anchors (210a, 210b, 310a, 310b) secure the devices (200, 300) at the treatment location. Although the figures illustrate two tissue anchors at the large end of the device (200, 300), one with ordinary skill in the art would understand that the number of tissue anchors on each device and locations of the tissue anchors on each device varies according to the anatomy of the treatment location, and needs of securing the device.

Figure 8:
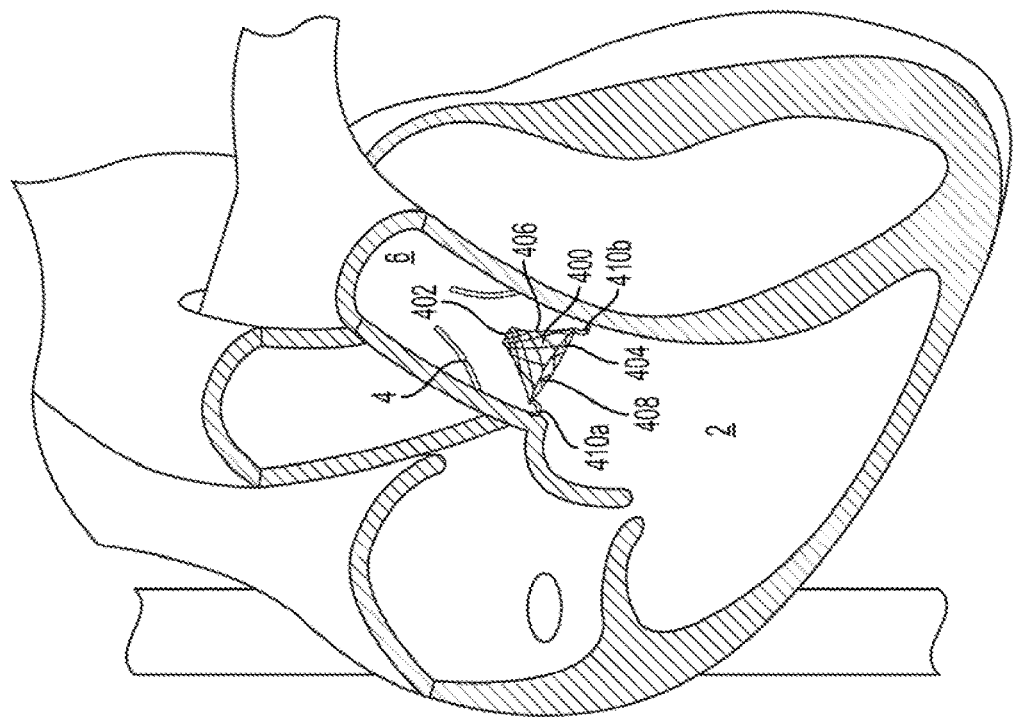
FIG. 8 is a perspective view of an exemplary medical device in accordance with the present teachings.

Now referring to another embodiment of the present teachings, an exemplary pulmonary valve intervention device (400) is implanted proximally to the pulmonary valve (4). As illustrated in FIG. 8, the device (400) is implanted at a treatment site proximally to the pulmonary valve (4), thereby restricting the blood flow to the pulmonary valve (4). As illustrated in FIG. 8, in its deployed configuration, the device (400) has a proximal end (404) having a diameter, as distal end (402) having a diameter smaller than the diameter of the proximal end, a tapered elongated tubular body with an outer surface (406) and a shunt (408) extending from the distal end (402) to the proximal end (404). The device (400) is configured such that all blood flowing from the right ventricle (2) toward the pulmonary valve (4) would enter from its proximal end (404), flow through the shunt (408), and exit from the distal end (402) of the device. According to one embodiment of the present teachings, the device (400) is configured to withstand a certain amount of pressure so that the amount of blood exiting the distal end (402) of the device (400) is less that the amount of the blood entering the proximal end (404) of the device (400).

During each pulmonary circulation, as oxygen-depleted blood fills the right ventricle (2), the pressure of the right ventricle (2) rises above the pressure in the pulmonary artery (6). As the right ventricle (2) contracts, the oxygen-depleted blood in the right ventricle (2) is forced into the proximal end (404) of the device (400), through the shunt (408), exits the distal end (402) of the device, pushes the pulmonary valve (4) open, and flows into the pulmonary artery (6). As blood empties from the right ventricle, the pressure of the right ventricle (2) drops, and as the blood fills the pulmonary artery (6), the pressure inside the pulmonary artery (6) rises. As illustrated in FIG. 8, with a pulmonary valve intervention device (4) implanted proximally to the pulmonary valve (4), the blood exiting the distal end (402) of the device is less than the amount of the blood entering: the proximal end (404) of the device, and thus the amount of the blood entering the lung through the pulmonary artery (6) is restricted by the device (400).

In one embodiment of the present teachings, as the size of the opening at the distal end (402) of the device (400) increases, the amount of the blood exiting the device (400) increase, the amount of blood allowed to enter the lung increases, and the blood flow restriction imposed by the device (400) decreases. In another embodiment, as the size of the opening at the distal end (402) of the device (400) decreases, the amount of blood allowed to enter the lung decreases, and the blood flow restriction imposed by the device (400) thus increases.

In one embodiment of the present teachings, the distal portion of the device (400) is configured to expand radially in responding, to the changes of the right ventricle (2.) pressure. Since the restriction to the blood flow will lead to an increase in the right ventricle (2) pressure, in order to prevent a right heart overload, the distal portion of the device (400) is designed to expand, or enlarge, as the right ventricle (2) pressure reaches a pre-defined limit. According to one embodiment, as the distal portion of the device (400) expands radially, the amount of the blood exiting the distal end (402) of the device (400) increases, and the restriction imposed by such device (400) is thus reduced. In one embodiment of the present teachings, when the right ventricle (2.) pressure reaches a pre-defined limit, for example, 50-80 mmHg, the distal portion of the device (400) will be forced to expand radially by the increased blood pressure, more blood then exits the distal end (402) of the device (400) and enters the pulmonary artery (6). This would lead to a pressure drop inside the right ventricle (2) to a safe range, such as 20-40 mmHg for a peak right ventricle systolic pressure.

According to one embodiment of the present teachings, the radial expansion of the distal portion of the device (400) is not reversible, so that once the distal portion of the device (400) expands radially, it will remain at the enlarged profile. In the event where the right ventricle (2) pressure continues to build up and reaches the pre-defined limit, the distal portion of the device (400) will expand further radially to prevent a right heart overload. As the distal portion of the device (400) reaches its maximum radial profile, the device (400) will imposes no restriction to the blood flow from the right ventricle (2) to the pulmonary artery (6).

According to other embodiments of the present teachings, the radial expansion of the distal portion of the device (400) is reversible, so that as the right ventricle (2) pressure drops below the pre-defined limit, the distal portion of the device (400) retracts to its original size. In the event where the right ventricle (2) pressure increases again and reaches the pre-defined limit, the opening at the distal portion of the device (400) will expand radially again, thereby allowing more blood to exit the distal end (402) of the device (400). In one embodiment of the present teachings, the greater is the right ventricle (2) pressure, the greater does the distal portion of the device (400) expand radially.

Figure 10:
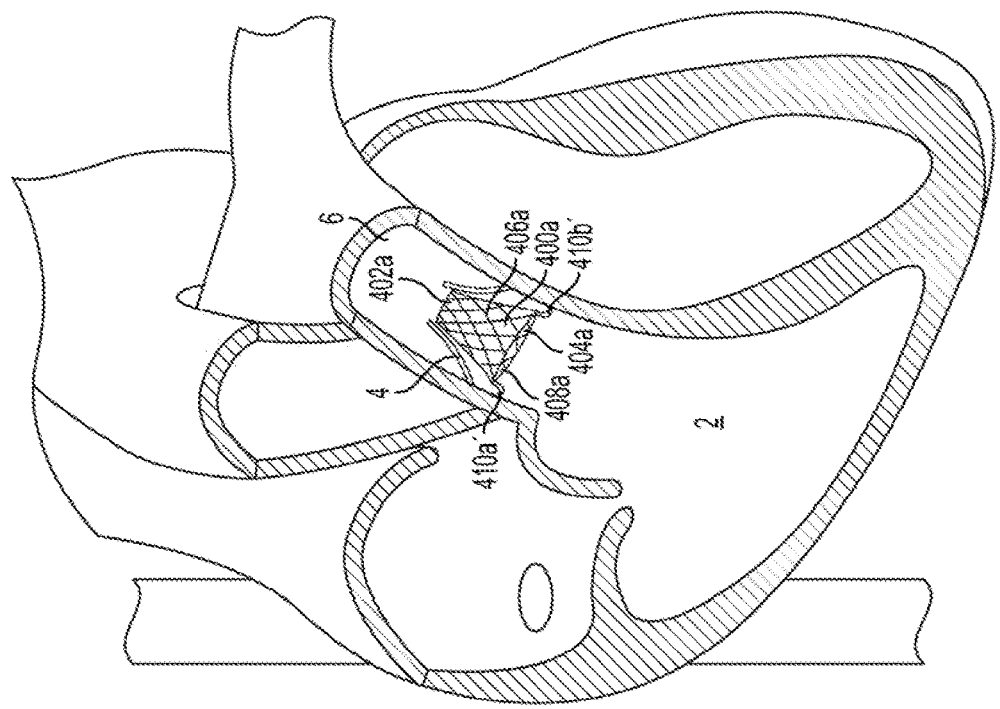
FIG. 10 is a perspective view of an exemplary medical device where a distal portion of the device has a opened mesh structure in accordance with the present teachings.
Figure 9:
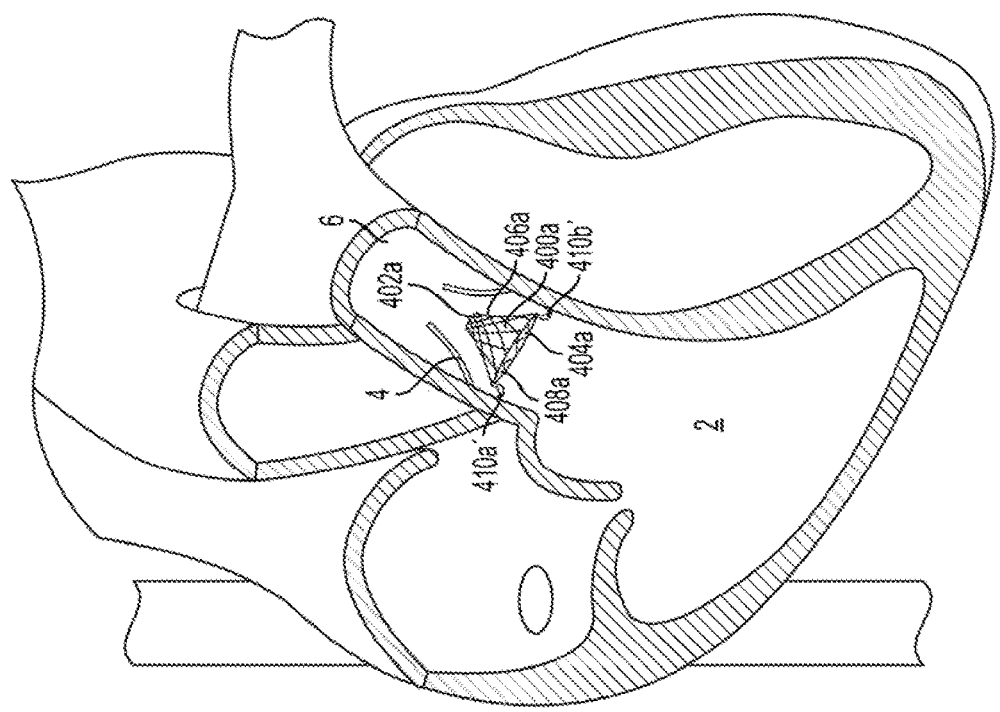
FIG. 9 is a perspective view of an exemplary medical device where a distal portion of the device has a closed mesh structure in accordance with the present teachings.

FIGS. 9-10 illustrate the radial expandability of the opening at the distal portion of the pulmonary valve intervention device (400a), according to one embodiment of the present teachings. As illustrated in FIG. 9, the radial expansion of the distal portion of the device (400a) is achieved by the mesh-like structure at the distal portion of the device (400a). In this embodiment, when the device (400a) is initially deployed at the treatment site, the mesh is closed so that the blood entering the proximal end (404a) of the device (400a) exits from the distal end (402a) of the device (400a). As the pressure inside the right ventricle (2) reaches a pre-defined limit, the blood pressure forces the mesh-like structure at the distal portion of the device to open, thereby expanding the opening of the distal portion of the device (400a). as illustrated in FIG. 10. At this point, the blood entering from the proximal end (404a) of the device (400a) could exits through the opened mesh and the distal end (402a) of the device (400a). This results in a lesser restriction to the blood flowing from the right ventricle (2) to the pulmonary artery (6).

Figure 11:
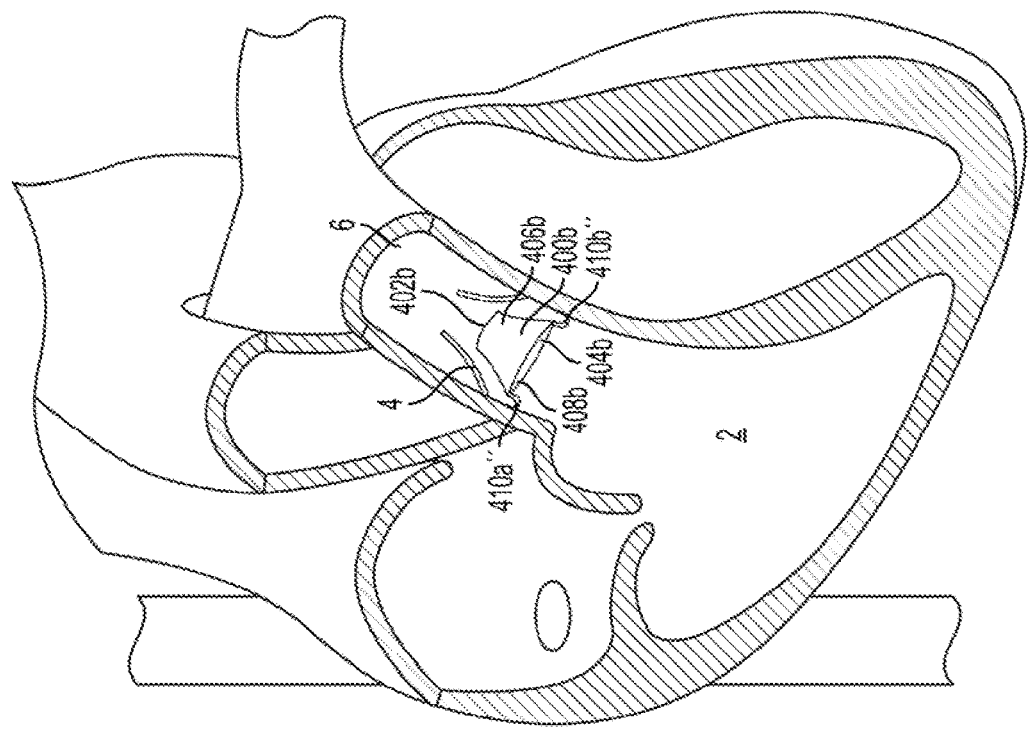
FIG. 11 is as perspective view of an exemplary medical device where a distal portion of the device has a folded structure in accordance with the present teachings.
Figure 12:
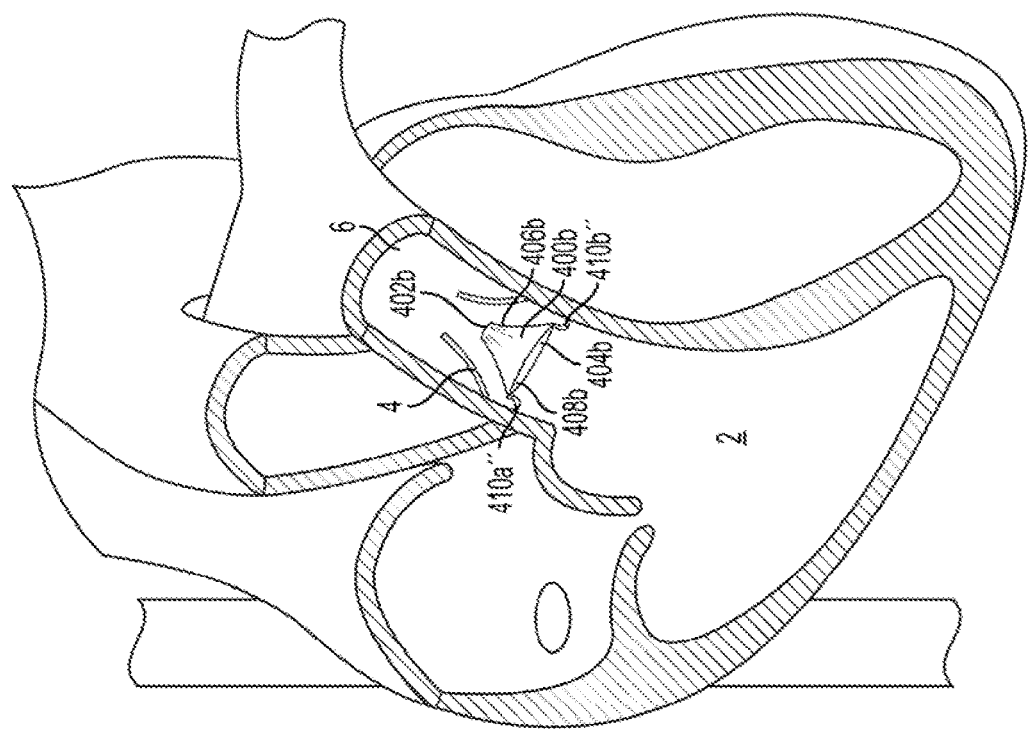
FIG. 12 is a perspective view of an exemplary medical device where a distal portion of the device has an unfolded structure in accordance with the present teachings.

FIGS. 11-12 illustrates the radial expandability of the opening at the distal portion of the pulmonary valve intervention device (400b), according to another embodiment of the present teachings. As illustrated in FIG. 11, the radial expansion of the distal portion of the device (400b) is achieved by a folded tubular surface at the distal portion of the device (400b). In this embodiment, when the device (400b) is initially deployed at the treatment site, the folds of the distal portion of the device (400b) is closed. As the pressure inside the right ventricle (2) reaches a pre-defined limit, the folded distal portion of the device (400b) is forced open and unfolds, and thereby expanding the opening of the distal portion of the device (400b), as illustrated in FIG. 12. At this point, more blood could exits from the distal end (402b) of the device (400b). This results in a lesser restriction to the blood flowing, from the right ventricle (2) to the pulmonary artery (6). It should be understood by those skilled in the field that other designs can be incorporated to enable the distal portion of the device to expand radially when the right ventricle (2) pressure reaches a pre-designed limit. Thus the specific embodiments presented herein should not be viewed as limiting.

Figure 13:
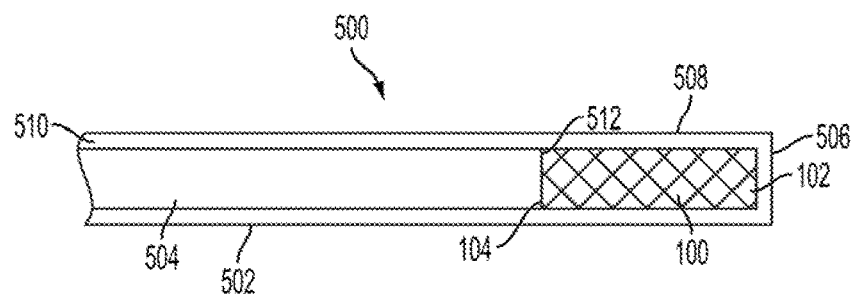
FIG. 13 is a perspective view of an exemplary medical device delivery system in accordance with the present teachings.

FIG. 13 depicts a use of an embodiment of the present teachings in conjunction with a delivery system (500), which can be manipulated externally by a clinician. For example, by inserting a portion of the delivery system (500) into a patient's body, a clinician can deliver an exemplary pulmonary valve intervention device (100) into the body. In one embodiment, the delivery system (500) includes a delivery sheath (502) having a distal end (506), a proximal end (not shown), and an axial lumen (510) extending from the distal end through the proximal end; and a delivery catheter (504) also having a distal end (512) and a proximal end (not shown) slidably disposed within the axial lumen (510) of the delivery sheath (502). Both the delivery sheath (502.) and the delivery catheter (504) can be manipulated by a clinician proximally. In this particular embodiment, a device (100), extended into its elongated delivery profile, is slidably disposed within a distal portion (508) of the delivery sheath (502), the distal end (102) of the device (100) is within the distal end (506) of the delivery sheath (502), and the proximal end (104) of the device (100) is in contact with the distal end (512) of the delivery catheter (504). The distal end (512) of the delivery catheter (504) is designed so as to contact the proximal end (104) of the device (100). The delivery catheter prevents the device from moving pro laity, or pushes the device (100) distally during a deployment.

Figure 14:
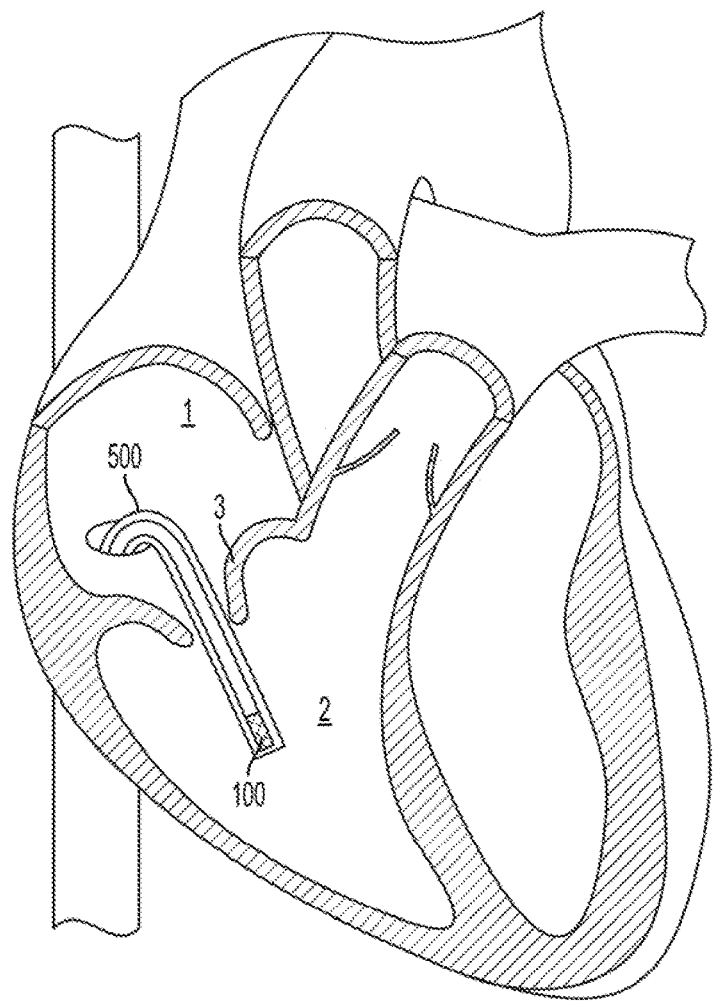
FIG. 14 is a perspective view of an exemplary medical device delivery system entering right ventricle in accordance with the present teachings.

FIGS. 14-17 depict steps for deploying an exemplary pulmonary valve intervention device (100) inside a heart. As illustrated in FIG. 14, in one embodiment of the present teachings, the clinician starts a standard right heart catheterization procedure by inserting a delivery system (500) percutaneously at an insertion point, holding the device (100) in its delivery profile, advancing distally through the femoral vein, the inferior vena cava, to the right atrium (I), then through the tricuspid valve (3) into the right ventricle (2). In the embodiment where the device (100) is designed to restrict the blood outflow to the pulmonary artery (6), the distal end of the delivery system (500) stops proximally to the pulmonary valve (4) annulus (not shown). In the embodiment where the device (100) is designed to allow blood to back-flow from the pulmonary artery (6) to the right ventricle (2), the distal end of the delivery system (500) further extends through the pulmonary valve (4) annulus into the pulmonary artery (6), and stops inside the pulmonary artery (6) distal to the pulmonary valve (4) (not shown). In some embodiments, a radio-opaque marker is used on the delivery sheath (502), the delivery catheter (504), or the implant device (100) to aid a clinician in determining how far the distal portion of the delivery assembly should extend. In other embodiments, as guide wire is used to locate the treatment site.

Figure 15:
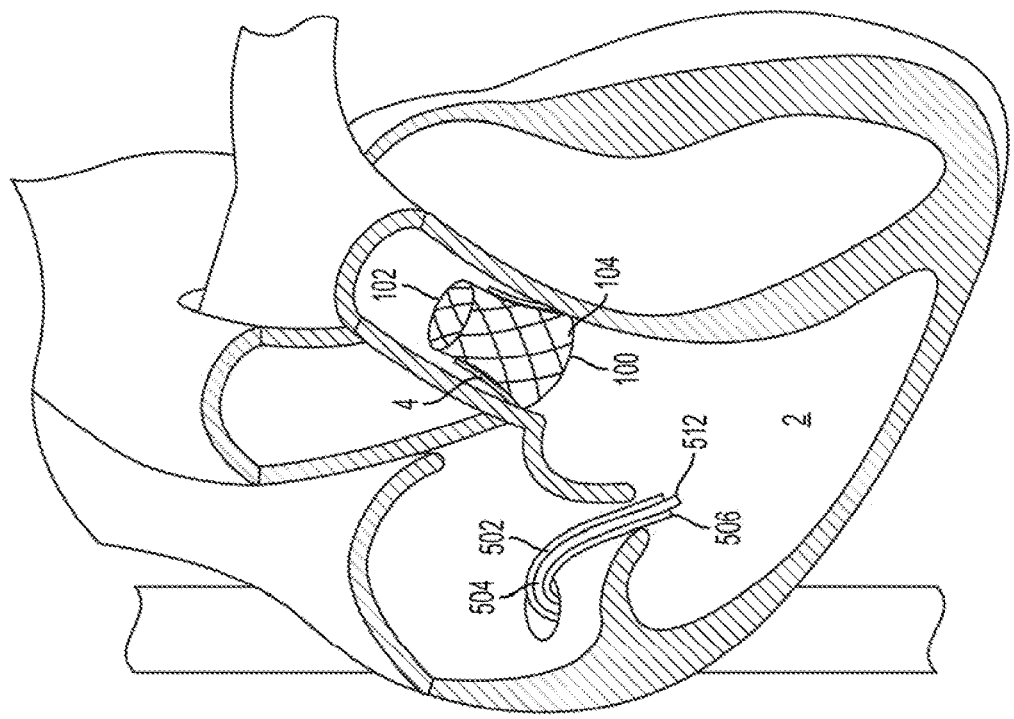
FIG. 15 is a perspective view of an exemplary medical device delivery system deploying an exemplary medical device in accordance with the present teachings.

Upon reaching a treatment site, the device (100) is deployed as illustrated in FIG. 15. According to one embodiment of the present teachings, the delivery sheath (502) is retracted proximally with respect to the delivery catheter (504) and the implant device (100) to expose the device (100) outside of the distal end (506) of the delivery sheath (502). According to an alternative embodiment, the deployment of the device (100) is accomplished by advancing the delivery catheter (504) distally with respect to the delivery sheath (502). As the delivery catheter (504) extends distally, the device(100) is pushed outside of the distal end (506) of the delivery sheath (502). As the device (100) is exposed outside of the delivery sheath (502), the device (100) resumes its pre-set deployed configuration and secures itself to the surrounding tissues. At this point, the entire delivery system (500), including the delivery sheath (502) and delivery catheter (504), is retracted proximally, and removed from the body.

In one embodiment of the present teachings, the distal end (512) of the delivery catheter (504) contacts but does not engage the proximal end (104) of the device (100) in such a way that allows the delivery catheter (504) to push the device (100) distally and prevent the device (100) from sliding proximally during a deployment. After the device (100) fully exits the delivery sheath (502), the delivery catheter (504) no longer controls the device (100). In this embodiment, once the device (100) is outside the delivery system (500), it is no longer controlled by the clinician.

In another embodiment of the present teachings, the delivery catheter (504) actively engages the device (100) during delivery and implantation. Such an engagement can be achieved by a mechanical means, magnetic means, or other methods known to those skilled in the art. Such an engagement requires releasing the device (100) by a clinician in order to free the implant device (100) from the delivery system (500). In one embodiment, after the device (100) fully exits the delivery sheath (502), the proximal end (104) of the device (100) is still been held by the delivery catheter (504) which allows the clinician to assess the deployment, the performance, and the securement of the device (100) to the surrounding tissue. When the deployment is deemed satisfactory, the clinician can then release the device (100) and remove the delivery system (500), including the delivery sheath (502) and the delivery catheter (504), from the body. If the deployment is not satisfactory, the clinician can remove the device (100) by pulling the device (100) proximally back into the delivery sheath (502), and then removing the delivery system (500), including delivery sheath (502) and delivery catheter (504), along with the device (100) from the body In one embodiment of the present teachings, the device (100) and the catheter are attached. The attachment between the delivery catheter (504) and device (100) can be in the form of any operator controllable or controlled mechanism, such as a threaded attachment, a ball and socket attachment, a ball and loop attachment, a ball-to-ball attachment, a pin-to-pin attachment, a tensioned clamp and ball attachment, a collet and ball attachment, a magnetic attachment member, or a releasable suture. It should be understood by those skilled in the field that other attachment mechanism can be incorporated here. According to one embodiment, the attachment between the delivery catheter (504) and the device (100) is reversible, That is, the attachment of the delivery catheter (504) to the device (100) can be reformed even after the device (100) is partially or completely released from such an attachment.

Figure 16:
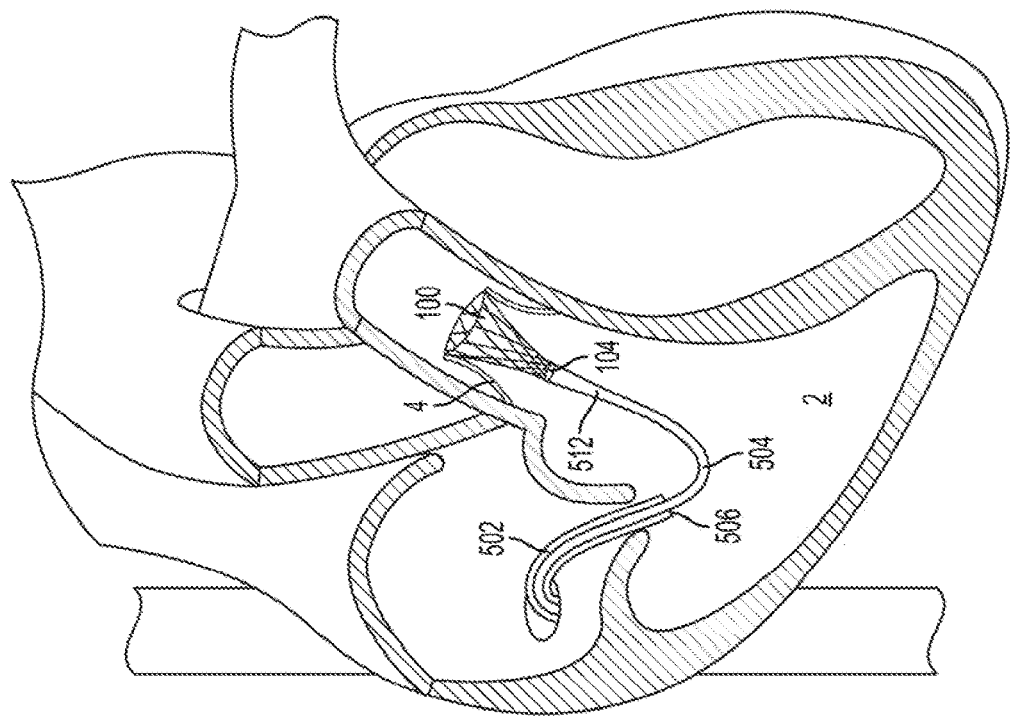
FIG. 16 is a perspective view of an exemplary medical device delivery system releasing an exemplary medical device in accordance with the present teachings.

FIG. 16 illustrates a last step in deploying the device (100). That is when the deployment is deemed satisfactory, the clinician can release the attachment between the delivery catheter (504) and the device (100). The delivery sheath (502) and the delivery catheter (504) can be removed from the body. According to some embodiments, if the deployment is not satisfactory, the device (100) can be retrieved via other techniques. It should be understood that the techniques disclosed herein for deploying the embodiments are only examples. Other techniques can be used instead of, or in combination with, these disclosures. For example, the techniques used to deploy an embodiment of the present teachings depend on the particular features of the device, the delivery system, and the anatomy in which the device is being deployed.

The methods and devices disclosed above are useful for treating one or more symptoms of diastolic heart failures by restricting the amount of blood flowing from the right ventricle to the pulmonary artery. One skilled in the art would further recognize that devices according to the present teachings could he used to regulate pressures in other parts of the heart and/or the vascular portions of the body. For example, the devices disclosed herein can he deployed in the renal artery to affect the sympathetic nervous system which controls fluid retention, or the coronary sinus and the carotid artery.

Various embodiments have been illustrated and described herein by way of examples, and one of ordinary skill in the art would appreciate that variations can he made without departing from the spirit and scope of the present teachings. The present teachings are capable of other embodiments or of being practiced or carried out in various other ways. Also, it is to he understood that the phraseology and terminology employed herein is for the purpose of description and should not be regarded as limiting.

Unless otherwise defined, all technical and scientific terms used herein have the same meaning as commonly understood by one of ordinary skill in the art to which this present teachings belong. Methods and materials similar or equivalent to those described herein can be used in the practice or testing of the present teachings. In case of conflict, the patent specification, including definitions, will control. In addition, the materials, methods, and examples are illustrative only and not intended to be limiting.

We claim:

1. A method of treating a patient with a diastolic heart failure by restricting blood flow from the right ventricle to the pulmonary artery comprising:
    providing a delivery system and an implantable device, wherein the delivery system comprises a proximal end, a distal end, and an axial lumen,
    wherein the implantable device comprises a distal end, a proximal end, and a hollow body portion, and
    wherein the implantable device has a first elongated profile when slidably disposed within the axial lumen of the delivery system, and a second expanded profile when the device is outside of the delivery system,
    advancing the delivery system and the implantable device in its first elongated profile at or near the pulmonary valve,
    deploying the distal end of the device at a location distal to the pulmonary valve annulus, the proximal end of the device at or near the pulmonary valve annulus, and the hollow body portion of the device through the pulmonary valve, and
    allowing blood back-flow from the pulmonary artery to the right ventricle.

2. The method of claim 1 comprising retracting the delivery system from the body.

3. The method of claim 1 comprising engaging at least one tissue anchor on the implantable device to the surrounding tissue.

4. The method of claim 1, wherein the implantable device, upon deployment, comprises a radially expandable distal portion with a first configuration and a second configuration, wherein the second configuration is radially expanded comparing to the first configuration, and
    wherein the method further comprises the distal portion of the implantable device transitions from the first configuration to the second configuration when the right ventricle reaches a set pressure.

5. The method of claim 1 further comprising allowing blood to outflow from the right ventricle through the hollowed body portion of the device to the pulmonary artery.

6. The method of claim 3, wherein the at least one tissue anchor on the implantable device engages the pulmonary valve annulus.

7. The method of claim 4, wherein the distal portion of the implantable device expands further radially when the right pressure continues to increase beyond the set pressure until the distal portion of the device reaches a maximum radial profile.

8. A method of treating a patient with diastolic heart failures by restricting blood flow from the right ventricle to the pulmonary artery comprising:
    providing an implantable medical device having a hollowed body portion with a distal end and a proximal end, wherein the device has an elongated delivery configuration and an expanded deployed configuration,
    advancing the implantable device in its elongated delivery profile at or near the pulmonary valve,
    deploying the distal end of the device at a location distal to the pulmonary valve annulus, the proximal end of the device at or near the pulmonary valve annulus, and the hollowed body portion of the device through the pulmonary valve, and
    allowing blood back-flow from the pulmonary artery to the right ventricle.

9. The method of claim 8 further comprising allowing blood to outflow from the right ventricle through the hollowed body portion of the device to the pulmonary artery.

10. The method of claim 8 further comprising engaging at least one tissue anchor on the implantable device to the surrounding tissue.

11. The method of claim 8, wherein the at least one tissue anchor on the implantable device engages the pulmonary valve annulus.

12. The method of claim 8, wherein the implantable device, upon deployment, comprises a radially expandable distal portion with a first configuration and a second configuration, wherein the second configuration is radially expanded comparing to the first configuration, and wherein the method further comprises the distal portion of the device transitions from the first configuration to the second configuration when the right ventricle reaches a set pressure.

13. The method of claim 12, wherein the distal portion of the device expands further radially when the right pressure continues to increase beyond the set pressure until the distal portion of the device reaches a maximum radial profile.

* * * * *